United States Patent
Kweon et al.

(10) Patent No.: US 12,427,204 B2
(45) Date of Patent: Sep. 30, 2025

(54) ANTIBODY-BOUND LIPID NANOPARTICLE COMPRISING ANTIBODY BOUND TO MEMBRANE SCAFFOLD PROTEIN

(71) Applicants: RESEARCH & BUSINESS FOUNDATION SUNGKYUNKWAN UNIVERSITY, Suwon-si (KR); MVRIX CO., LTD., Hwaseong-si (KR)

(72) Inventors: Dae-Hyuk Kweon, Seoul (KR); Wonbeom Park, Seoul (KR); Suhyun Kim, Seoul (KR)

(73) Assignees: RESEARCH & BUSINESS FOUNDATION SUNGKYUNKWAN UNIVERSITY, Suwon-si (KR); MVRIX CO., LTD., Hwaseong-si (KR)

( * ) Notice: Subject to any disclaimer, the term of this patent is extended or adjusted under 35 U.S.C. 154(b) by 0 days.

(21) Appl. No.: 18/833,679

(22) PCT Filed: Jan. 27, 2023

(86) PCT No.: PCT/KR2023/001298
§ 371 (c)(1),
(2) Date: Aug. 27, 2024

(87) PCT Pub. No.: WO2023/146356
PCT Pub. Date: Aug. 3, 2023

(65) Prior Publication Data
US 2025/0152732 A1    May 15, 2025

(30) Foreign Application Priority Data

Jan. 28, 2022   (KR) .................. 10-2022-0013592
Jan. 26, 2023   (KR) .................. 10-2023-0010355

(51) Int. Cl.
*A61K 48/00*    (2006.01)

(52) U.S. Cl.
CPC .......................... *A61K 48/0033* (2013.01)

(58) Field of Classification Search
None
See application file for complete search history.

(56) References Cited

U.S. PATENT DOCUMENTS

| 2009/0257950 A1* | 10/2009 | Sligar | ..................... A61P 31/12 |
| | | | 514/23 |
| 2019/0255145 A1 | 8/2019 | Kweon et al. | |
| 2022/0372496 A1* | 11/2022 | Kweon | ................. C12N 15/62 |

FOREIGN PATENT DOCUMENTS

| CN | 110960688 A | 4/2020 |
| JP | 2004-513653 A | 5/2004 |

(Continued)

OTHER PUBLICATIONS

Yunching Chen, Xiaodong Zhu, Xiaoju Zhang, Bin Liu and Leaf Huang. "Nanoparticles Modified With Tumor-targeting scFv Deliver siRNA and miRNA for Cancer Therapy." Molecular Therapy, vol. 18, No. 9, Sep. 2010, pp. 1650-1656. (Year: 2010).*

(Continued)

*Primary Examiner* — Isaac Shomer
(74) *Attorney, Agent, or Firm* — Sughrue Mion, PLLC

(57) ABSTRACT

The present invention relates to an antibody-bound lipid nanoparticle comprising an antibody conjugated with a membrane scaffold protein, and more specifically relates to an antibody-bound lipid nanoparticle which comprises a lipid, and an antibody conjugated with a membrane scaffold protein, and which can be easily produced and has an excellent specific targeting ability.

5 Claims, 16 Drawing Sheets

Specification includes a Sequence Listing.

(56) References Cited

FOREIGN PATENT DOCUMENTS

| | | | | |
|---|---|---|---|---|
| JP | 2007-525490 A | 9/2007 | | |
| KR | 10-0953917 B1 | 4/2010 | | |
| KR | 10-1343791 B1 | 12/2013 | | |
| KR | 10-2018-0008338 A | 1/2018 | | |
| KR | 20180008338 A | * | 1/2018 | ............ A61K 39/12 |
| KR | 10-1933199 B1 | 12/2018 | | |
| KR | 10-2019-0050586 A | 5/2019 | | |
| KR | 10-2019-0093816 A | 8/2019 | | |
| KR | 10-2021-0035753 A | 4/2021 | | |
| KR | 20210035753 A | * | 4/2021 | ........... C07K 14/705 |
| KR | 10-2021-0085296 A | 7/2021 | | |
| KR | 10-2021-0124898 A | 10/2021 | | |
| WO | 2016/167367 A1 | 10/2016 | | |
| WO | 2021/060791 A1 | 4/2021 | | |

OTHER PUBLICATIONS

Linde Schoenmaker et al. "mRNA-lipid nanoparticle COVID-19 vaccines: Structure and stability." International Journal of Pharmaceutics, vol. 601, 2021, Article 120586, pp. 1-13. (Year: 2021).*

JN Israelachvili, S Marcelja and RG Horn. "Physical Principles of Membrane Organization." Quarterly Reviews of Biophysics, vol. 13(2), 1980, pp. 121-200. (Year: 1980).*

English Translation of KR 20180008338 A. "Nano-perforator and Pharmaceutical Composition Comprising the Same for Preventing or Treating Viral Infection." Originally published in Korean on Jan. 24, 2018, 13 printed pages. (Year: 2018).*

English Translation of KR 20210035753 A. "Nano-Perforator Having Enhanced Antiviral Activity." Originally published in Korean on Apr. 1, 2021, 36 printed pages. (Year: 2021).*

Hideki Chiba, Makoto Osanai, Masaki Murata, Takashi Kojima, and Norimasa Sawada. "Transmembrane proteins of tight junctions." Biochimica et Biophysica Acta, vol. 1778, (2008) pp. 588-600. (Year: 2008).*

Nuphar Veiga et al., "Cell specific delivery of modified mRNA expressing therapeutic proteins to leukocytes," Nature Communications, 2018, vol. 9, 9 pages.

Kelsey L. Swingle et al., "Lipid Nanoparticle-Mediated Delivery of mRNA Therapeutics and Vaccines," Trends in Molecular Medicine, Jun. 2021, vol. 27, No. 6, pp. 616-617, 2 pages.

Korean Office Action in Korean Application No. 10-2023-0010355 dated Feb. 20, 2024.

International Search Report for International Application No. PCT/KR2023/001298 dated Apr. 26, 2023.

Written Opinion of the International Searching Authority in International Application No. PCT/KR2023/001298 dated Apr. 26, 2023.

Decision to Grant Patent in Korean Patent Application No. 10-2023-0010355 dated Aug. 6, 2024.

Kedmi et al., "A modular platform for targeted RNAi therapeutics", Nature Nanotechnology, vol. 13, Mar. 2018, pp. 214-219 (8 pages total).

Communication issued Apr. 17, 2025 in Chinese Application No. 202380024472.8.

Search Report issued Apr. 17, 2025 in Chinese Application No. 202380024472.8.

Federica Sebastiani, et al. "Apolipoprotein E Binding Drives Structural and Compositional Rearrangement of mRNA-Containing Lipid Nanoparticles", ACS Nano, 2021, vol. 15, pp. 6709-6722 (14 pages).

David M. Iovannisci, et al. "Targeting nanodisks via a single chain variable antibody- apolipoprotein chimera", Biochem Biophys Res Commun. Feb. 6, 2009, vol. 379, No. 2, pp. 466-469 (9 pages).

Japanese Office Action dated Jul. 22, 2025 in Application No. 2024-544982.

Chinese Office Action dated Aug. 15, 2025 in Application No. 202380024472.8.

* cited by examiner

FIG. 10

| Sample | Free mRNA (µg/mL) | Total mRNA (µg/mL) | Encapsulation (%) |
|---|---|---|---|
| LNP only | 0.5 | 11.5 | 95.9 |
| Early | 5.8 | 11.1 | 47.5 |
| Middle | 5.3 | 10.6 | 49.9 |
| Late | 3.9 | 10.3 | 62.7 |
| Total | 3.3 | 11.4 | 70.6 |

(a) A549 (10 % FBS, Target ligand X)

(b) MutuDC1940 (10 % FBS, Target ligand O)

ANTIBODY-BOUND LIPID NANOPARTICLE COMPRISING ANTIBODY BOUND TO MEMBRANE SCAFFOLD PROTEIN

CROSS REFERENCE TO RELATED APPLICATIONS

This is a National Stage Application of International Application No. PCT/KR2023/001298 filed Jan. 27, 2023, claiming priority based on Korean Patent Application Nos. 10-2022-0013592 filed Jan. 28, 2022 and 10-2023-0010355 filed Jan. 26, 2023.

INCORPORATION BY REFERENCE OF SEQUENCE LISTING

The content of the electronically submitted sequence listing, file name: Q300917_sequence listing as filed.XML; size: 45,719 bytes; and date of creation: Jul. 26, 2024, filed herewith, is incorporated herein by reference in its entirety.

TECHNICAL FIELD

The present invention relates to an antibody-bound lipid nanoparticle containing an antibody-conjugated membrane scaffold protein, and more specifically, to an antibody-bound lipid nanoparticle that contains a lipid and an antibody-conjugated membrane scaffold protein and thus can be easily prepared and has excellent specific target ability.

BACKGROUND ART mRNA acts to deliver genetic information from DNA to the organ that synthesizes proteins in the cytoplasm. When this mRNA enters the cell, protein is synthesized within the cell and an immune response occurs.

mRNA vaccines are being developed using mRNA having this property. However, mRNA has the problems that gene expression is suppressed due to interference caused by the immune response and it is difficult for the mRNA to enter the cytoplasm due to the large size thereof.

In an attempt to address these problems, lipid nanoparticles (LNP) have been developed to facilitate mRNA entrance to the cytoplasm and the value thereof is increasing as they are recently used as carriers for mRNA vaccines. However, the method of delivering lipid nanoparticles (LNPs) selectively to cells remains insufficient.

Accordingly, lipid nanoparticles with excellent target delivery ability have been developed by combining the excellent target delivery ability of antibodies with lipid nanoparticles. Conventional methods use chemical conjugation, thus disadvantageously making the overall process complicated and the yield low. In addition, conventional methods have a disadvantage in which the chemical identity is unclear and an affinity tag is attached to the antibody and thus it is thus difficult to identify the binding when injected in vivo.

DISCLOSURE

Technical Problem

Therefore, it is an object of the present invention to provide an antibody-bound lipid nanoparticle that can be prepared in a simple manner using an antibody that can bind to a lipid nanoparticle (LNP) and has excellent target delivery ability and a method of producing the same.

Technical Solution

In accordance with one aspect of the present invention, provided is an antibody-bound lipid nanoparticle in which an antibody or antibody fragment conjugated with a membrane scaffold protein is bound to a hydrophobic moiety of a lipid constituting a lipid nanoparticle via the membrane scaffold protein through a hydrophobic bond.

In the antibody-bound lipid nanoparticle of the present invention, the membrane scaffold protein is preferably an amphipathic protein having a helix structure.

In this case, the membrane scaffold protein may be a fragment of the membrane scaffold protein that maintains the helix structure and amphipathic property.

In the antibody-bound lipid nanoparticle of the present invention, the antibody fragment is preferably scFv or scFV-Fc.

In the antibody-bound lipid nanoparticle of the present invention, the antibody or antibody fragment conjugated with the membrane scaffold protein is preferably produced by binding a gene encoding the antibody or antibody fragment to a gene encoding the membrane scaffold protein and expressing the result.

In the antibody-bound lipid nanoparticle of the present invention, the lipid nanoparticle preferably contains a substance encapsulated therein. In this case, the encapsulated substance is preferably nucleic acid.

In accordance with another aspect of the present invention, provided is a method of producing an antibody-bound lipid nanoparticle by mixing a membrane scaffold protein-conjugated antibody with a lipid.

In the method, the antibody-bound lipid nanoparticle is preferably further mixed with an encapsulated substance.

Advantageous Effects

The antibody-bound lipid nanoparticle according to the present invention contains a membrane scaffold protein-conjugated antibody, thus exhibits excellent specific delivery ability to target cells and can be easily prepared.

DESCRIPTION OF DRAWINGS

FIG. 10 shows the mRNA encapsulation (%) of the antibody-bound lipid nanoparticle at each mixing time, while the antibody of the present invention is mixed during the process of forming lipid nanoparticles, in order to optimize the mixing time of the lipid nanoparticle with the antibody of the present invention.

BEST MODE

The present invention provides an antibody-bound lipid nanoparticle in which an antibody or antibody fragment conjugated with a membrane scaffold protein is bound to a hydrophobic moiety of a lipid constituting a lipid nanoparticle via the membrane scaffold protein through a hydrophobic bond.

Figure 1:
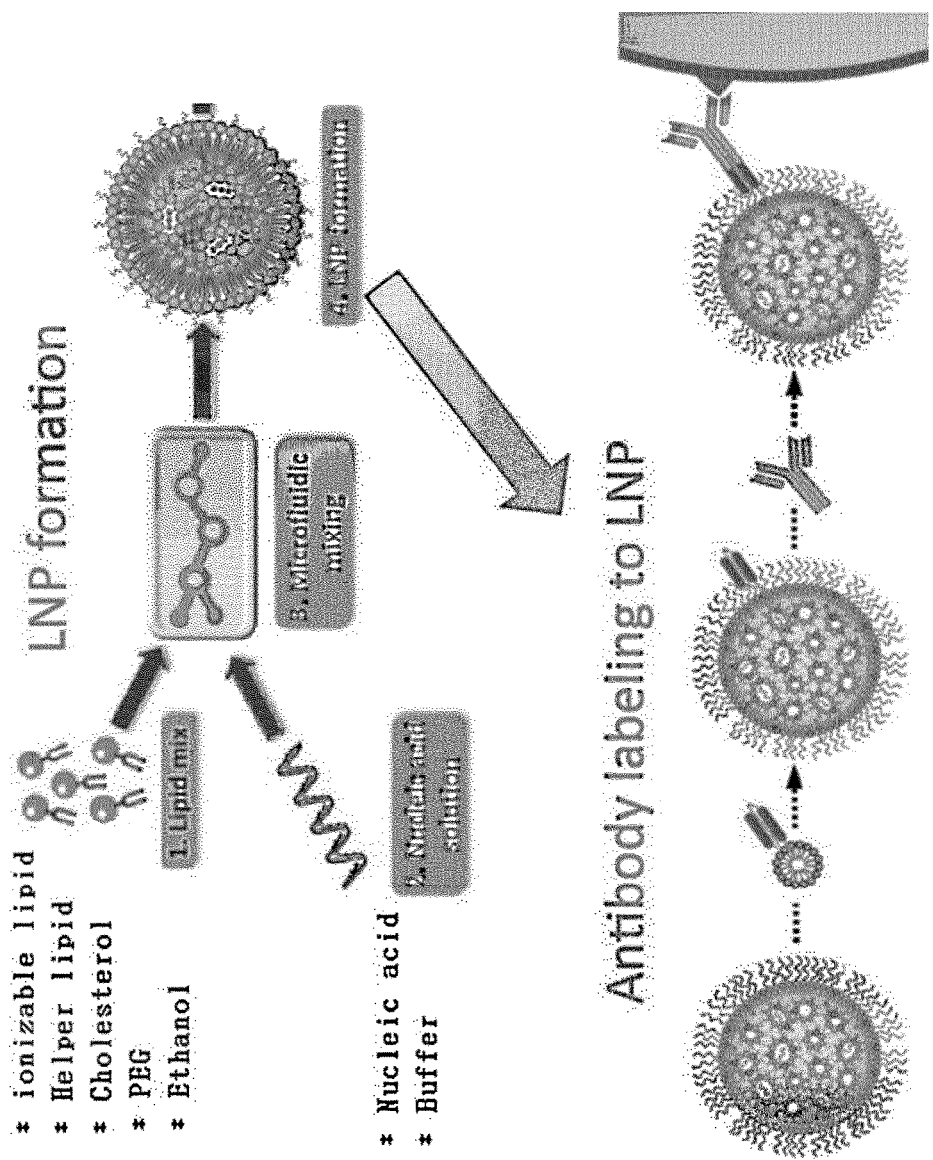
FIG. 1 is a schematic diagram illustrating conventional method of producing antibody-bound lipid nanoparticles.

A conventional method of producing antibody-bound lipid nanoparticles (having a configuration in which antibodies are bound to the surface of lipid nanoparticles) includes the following steps: 1) mixing a lipid mixture constituting a lipid nanoparticle with an encapsulated substance to produce a lipid nanoparticle; 2) binding the lipid nanoparticle to a compound capable of binding to an antibody; and 3) binding an antibody to the compound, and thus includes at least three steps (see FIG. 1).

Figure 2:
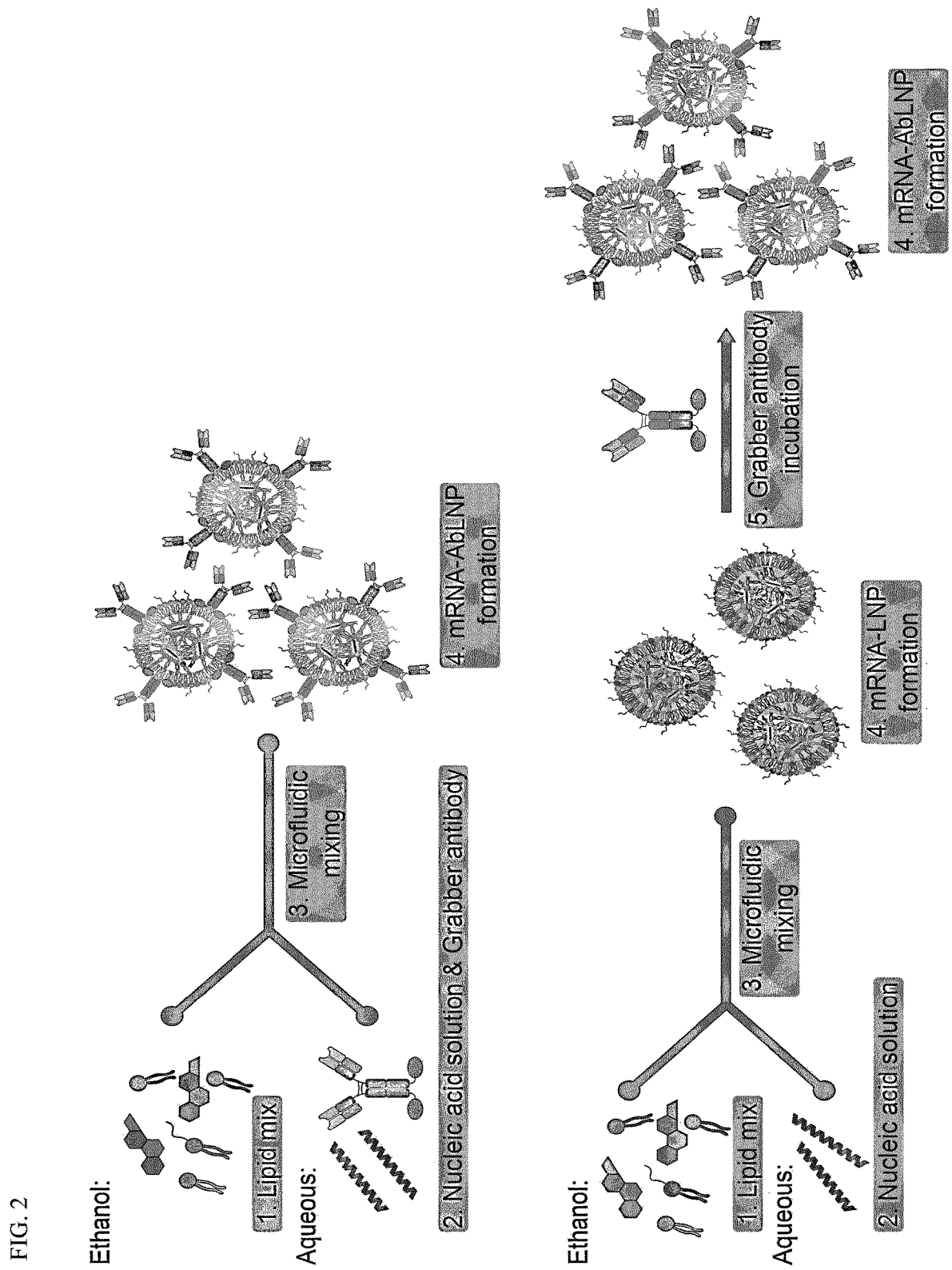
FIG. 2 is a schematic diagram illustrating a method of producing an antibody-bound lipid nanoparticle using the antibody (grabber antibody) of the present invention. Meanwhile, the top diagram of FIG. 2 illustrates a method of producing an antibody-bound lipid nanoparticle by mixing with the antibody (grabber antibody) of the present invention while producing the lipid nanoparticle, and the bottom diagram of FIG. 2 illustrates a method of producing an antibody-bound lipid nanoparticle by adding the antibody (grabber antibody) of the present invention to the produced lipid nanoparticle.
Figure 3:
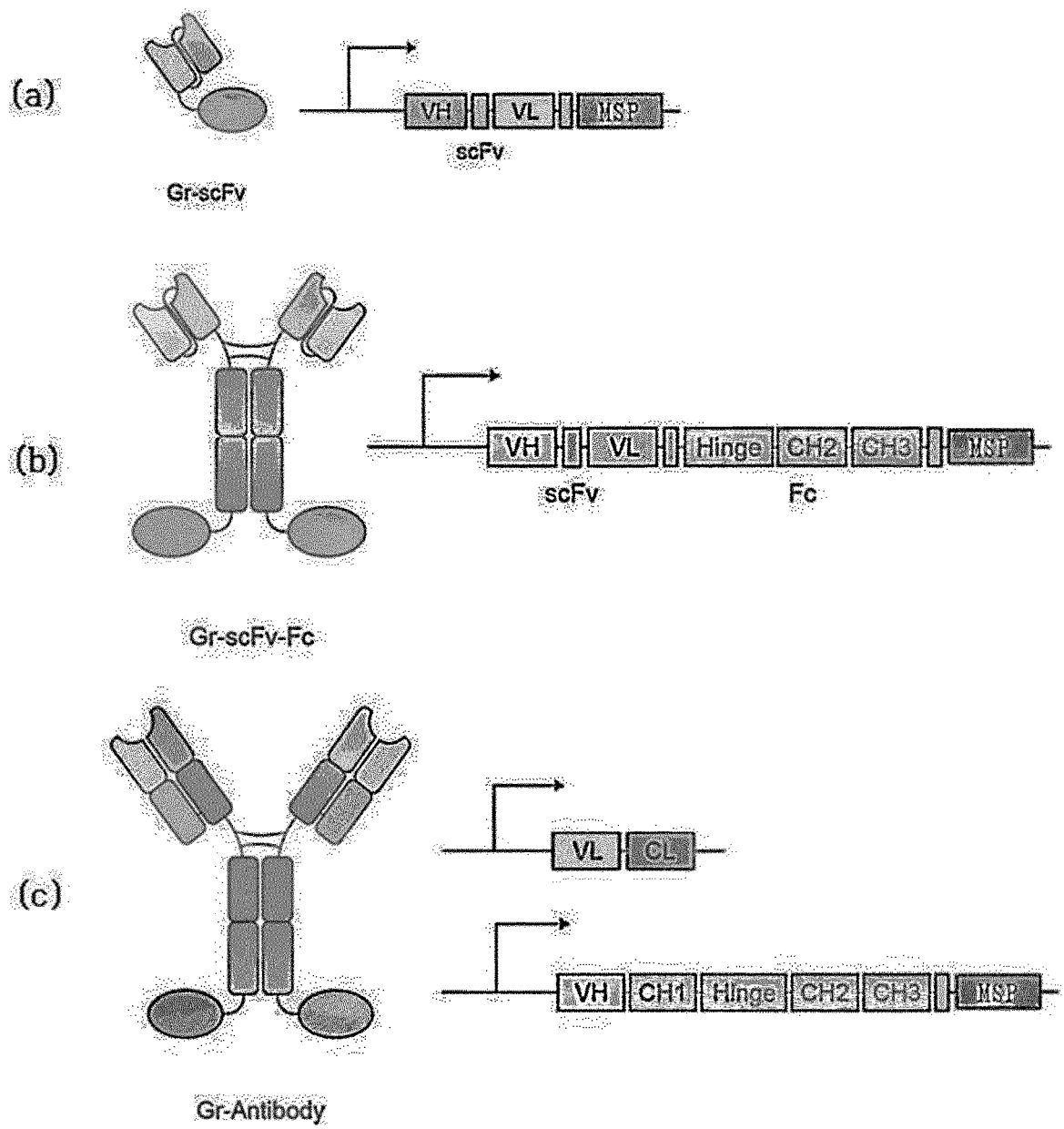
FIG. 3 is a schematic diagram illustrating the structure of the antibody (grabber antibody) of the present invention.

However, in the present invention, antibody-bound lipid nanoparticles can be produced without a separate antibody-binding process using an antibody conjugated with a membrane scaffold protein (see FIG. 3). That is, when the encapsulated substance, the lipid mixture, and the antibody of the present invention (so-called "grabber antibody") were mixed, the lipid nanoparticle is formed and at the same time, the antibody conjugated with the membrane scaffold protein was disposed on the surface of the lipid particle to obtain the antibody-bound lipid nanoparticle (see the top diagram of FIG. 2). This means that, when using an antibody conjugated with a membrane scaffold protein, the conventional three-step production process can be simplified into a one-step process.

In addition, it was found that antibody-bound lipid nanoparticles were produced by adding the antibody (so-called "grabber antibody") of the present invention to the produced lipid nanoparticles (see the bottom diagram of FIG. 2). This means that specificity can be imparted to lipid nanoparticles by modifying lipid nanoparticles with antibodies merely by simple addition without changing the conventional lipid nanoparticle production process.

Meanwhile, in the present invention, the membrane scaffold protein (MSP) is a protein that has a helix structure, is amphipathic, and acts to mediate the lipid and antibody of the antibody-bound lipid nanoparticle of the present invention. In this case, the membrane scaffold protein binds to the hydrophobic moiety of the lipid that constitutes the lipid nanoparticle based on a hydrophobic bond.

A representative example of the membrane scaffold protein is apolipoprotein. Apolipoprotein is a protein that is present specifically in plasma lipoproteins and is known to stabilize the structure of lipoproteins, activate enzymes involved in lipoprotein metabolism, and act as a ligand for lipoprotein receptors present on the cell surface. The apolipoprotein is, for example, apolipoprotein A1 (ApoA-I), apolipoprotein A2 (ApoA-2), apolipoprotein B (ApoB), apolipoprotein C (ApoC), apolipoprotein E (ApoE), MSP1

(membrane scaffold protein 1), MSP1D1, MSP1D2, MSP1E1, MSP1E2, MSP1E3, MSP1E3D1, MSP2, MSP2N1, MSP2N2, MSP2N3, or the like.

Apo-A1, which is mentioned as an example of apolipoprotein, is a protein that is composed of a 28 kDa single polypeptide containing 243 amino acids, has 8 repeating unit domains consisting of 11 amino acids or 22 amino acids, and has 60 to 75% of an alpha-helix proportion with a secondary structure constituting HDL. It is known that ApoA-I is mainly used as a component of high-density lipoprotein (HDL), which acts to remove cholesterol from surrounding tissues and deliver the cholesterol to the liver or other lipoproteins. In addition, ApoE is a protein that is composed of a 33 kDa single polypeptide consisting of 299 amino acids and mediates the delivery of cholesterol like ApoA1.

In addition, in the present invention, a fragment of the membrane scaffold protein that maintains the helix structure and amphipathic properties may be used as the membrane scaffold protein. In other words, a part (fragment) of the membrane scaffold protein, rather than the entire membrane scaffold protein, may be used as long as the helix structure and amphipathic properties of the membrane scaffold protein are not lost.

Meanwhile, in the present invention, the antibody or antibody fragment binds to lipid nanoparticles and serves to impart specific targeting ability to the target cell to which the antibody or antibody fragment may be bound. The antibody-bound lipid nanoparticles of the present invention may use various antibodies or antibody fragments depending on the characteristics of the target cell. In this case, the antibody fragment is preferably scFv, or scFv bound with scFv and Fc to provide specific targeting ability.

Meanwhile, in the present invention, the antibody conjugated with the membrane scaffold protein may be produced by binding a gene encoding the antibody to a gene encoding the membrane scaffold protein, and then expressing the result.

Meanwhile, the antibody-bound lipid nanoparticle of the present invention preferably contains a substance encapsulated therein. In this case, the encapsulated substance is preferably a nucleic acid. The nucleic acid is, for example, mRNA.

Lipid nanoparticles are mainly used to safely deliver the encapsulated substance to the target. Foreign mRNA has the problems in which gene expression is suppressed due to interference with the human's immune response and it is difficult to induce foreign mRNA into cells due to the large size thereof. The mRNA vaccine solves these problems using lipid nanoparticles and the antibody-bound lipid nanoparticles developed in the present invention may also be used as a carrier to deliver the mRNA vaccine.

Lipid nanoparticles are preferably prepared by mixing an ionizable lipid, a structural helper lipid, cholesterol, and polyethylene glycol. The lipid nanoparticles thus prepared are easily encapsulated in drugs such as nucleic acids, easily pass through cell membranes, and have excellent retention in the body.

In another aspect, the present invention provides a method of producing an antibody-bound lipid nanoparticle by mixing a membrane scaffold protein-conjugated antibody with a lipid.

As described above, the method according to the present invention is capable of simplifying the conventional three-step production process into a one-step production process using the membrane scaffold protein-conjugated antibody.

Meanwhile, in the method of producing the antibody-bound lipid nanoparticles of the present invention, the antibody-bound lipid nanoparticles are preferably further mixed with an encapsulated substance. The encapsulated substance is an mRNA vaccine. In this case, the antibody-bound lipid nanoparticles may be used as a carrier to transport the mRNA vaccine.

Hereinafter, the present invention will be described in more detail with reference to the following examples. The scope of the present invention is not limited to the examples and encompasses modifications of the technical concept equivalent thereto.

Example 1: Production of Plasmid for Producing Antibodies for Forming Lipid Nanoparticles In this example, an attempt was made to produce a plasmid capable of producing an antibody for forming lipid nanoparticles of the present invention.

1-1. Production of Plasmids for Producing Single Chain Antibody Fragments (Grabber Single Chain Variable Fragment, Gr-scFv) for Forming Lipid Nanoparticles Cloning was performed using pET-22b(+) or pcDNA3.1 (+) as a vector and T4 DNA polymerase to prepare a plasmid for producing a single-chain antibody fragment (Gr-scFv, see (a) in FIG. 3) for forming lipid nanoparticles that consists of a variable region of heavy chain (VH), a variable region of light chain (VL), and a membrane scaffold protein (MSP).

Specifically, PCR was performed using primers designed such that the pET-22b(+) or pcDNA3.1(+) vector is complementary to 15 bp of both ends of the VH-linker-VL-linker-Apolipoprotein insert. Then, the result was treated with DpnI enzyme for 2 hours at 37° C. to remove the methylated backbone plasmid for PCR. The result was reacted with T4 DNA polymerase at 25° C. for 150 seconds and on ice for 10 minutes to induce hydrogen bonding between the vector and the insert. 1 µL of the reaction product was mixed with 100 µL of *Escherichia coli* TOP10 competent cells, incubated on ice for 30 minutes, and heat-shocked at 42° C. for 45 seconds for gene transduction. Then, 900 µL of SOC (super optimal broth with catabolite repression) liquid medium was added to the result, followed by incubation at 37° C. for 1 hour, and centrifugation (13,000 rpm, 1 minute) to obtain cells. The obtained cells were resuspended in 100 µL of SOC liquid medium, plated on carbenicillin LB (Luria-Bertani) solid medium, and incubated at 37° C. for 16 hours to form colonies. The colonies were inoculated into LB liquid medium containing 100 µg/mL of carbenicillin and incubated at 37° C. for 16 hours, and then the plasmid for producing single-chain antibody fragments for forming lipid nanoparticles was purified using a plasmid purification kit.

1-2. Production of Plasmids for Producing Single Chain Antibodies (Grabber Single Chain Variable Fragment-Fc, Gr-scFv-Fc) for Forming Lipid Nanoparticles A plasmid for producing a single chain antibody for forming lipid nanoparticles was produced in the same manner as in Example 1-1 using a pcDNA3.1(+) vector and a VH-linker-VL-hinge-Fc-linker-apolipoprotein insert to produce a plasmid for producing single chain antibody for forming lipid nanoparticles (Gr-scFv-Fc, see (b) in FIG. 3) that consists of a variable region of heavy chain (VH), a variable region of light chain (VL), a fragment crystallizable region (Fc region), and a membrane scaffold protein (MSP).

1-3. Production of Plasmids for Producing Antibodies (Gr-Antibodies) for Forming Lipid Nanoparticles Plasmids for producing an antibody that forms lipid nanoparticles were produced in the same manner as in Example 1-1 using the pMAZ vector, VH-CH-linker-apolipoprotein, or VL-CL insert in order to produce a plasmid consisting of a variable region of heavy chain (VH), a constant region of heavy chain (CH), and a membrane scaffold protein (MSP), and a plasmid consisting of a variable region of light chain (VL) and a constant region of light chain (CL), as plasmids for producing an antibody (Gr-antibody, see (c) of FIG. 3) that forms lipid nanoparticles.

Example 2: Production of Antibodies for Forming Lipid Nanoparticles

In this example, the antibody for forming lipid nanoparticles according to the present invention was produced using the plasmid produced in Example 1.

2-1. Production of Single Chain Antibody Fragment (Grabber Single Chain Variable Fragment, Gr-scFv) for Forming Lipid Nanoparticles In order to produce single chain antibody fragments (grabber single chain variable fragment, Gr-scFv) for forming lipid nanoparticles having the protein sequences of SEQ ID NOS. 1 to 9, the plasmid using the pET-22b(+) vector produced in Example 1-1 was expressed using the *E. coli* protein expression system.

Specifically, the plasmid was injected into the expression host, *E. coli* BL21 (DE3) at 42° C., plated on carbenicillin LB (Luria-Bertani) solid medium at a concentration of 100 µg/mL, and incubated at 37° C. for 16 hours to form colonies and the transformed *E. coli* strains were selected. Each transformed strain was inoculated into LB liquid medium containing 100 µg/mL of carbenicillin, cultured at 37° C. for 16 hours, and then subcultured. The subculture solution was incubated until the optical density ($OD_{600}$) measured at a wavelength of 600 nm reached 1.5, and 0.5 mM IPTG (isopropyl β-D-1-thiogalactopyranoside) was added thereto, followed by culture at 25° C. for 6 hours to express single-chain antibody fragments that form lipid nanoparticles. Then, the culture solution was centrifuged (4,000 rpm, 10 minutes) to obtain cells. The obtained cells were pulverized using a sonicator and separated into soluble and insoluble fractions through centrifugation (15,000 rpm, 10 minutes).

Figure 4:
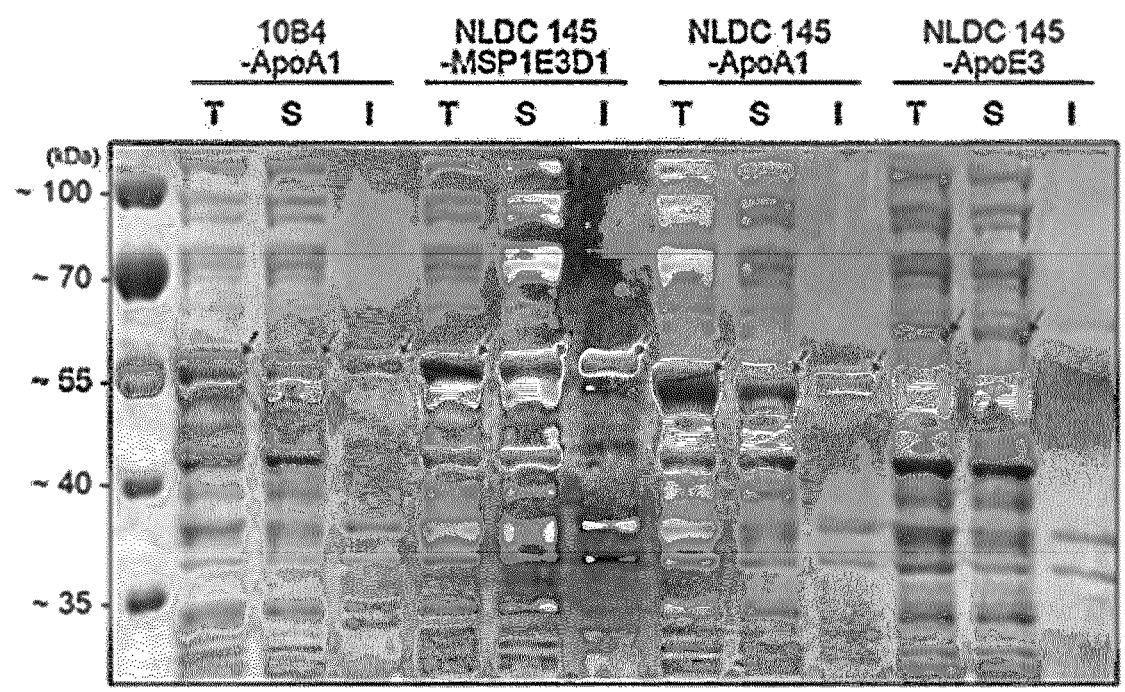
FIG. 4 shows the result of SDS gel electrophoresis to identify production of a single chain antibody fragment (grabber single chain variable fragment, Gr-scFv) of the present invention using an *E. coli* protein expression system, wherein 10B4 and NLDC 145 represent the antibodies used, and ApoA1, MSP1E3D1, and ApoeE3 represent the membrane scaffold proteins used.

Meanwhile, the proteins in each fraction were detected by SDS gel electrophoresis. The result showed that the single chain antibody fragment for forming lipid nanoparticles of the present invention was produced intact (FIG. 4). Meanwhile, in FIG. 4, 10B4 and NLDC 145 represent the antibodies used, and ApoA1, MSP1E3D1, and ApoeE3 represent the membrane scaffold proteins used.

In addition, in order to produce single-chain antibody fragments for forming lipid nanoparticles, the plasmid using the pcDNA3.1(+) vector produced in Example 1-1 was expressed using a mammalian cell protein expression system.

Specifically, HEK-293F (human embryonic kidney 293F) used as an expression host was incubated in an aqueous suspended cell state at 37° C. and 120 rpm in the presence of 8% $CO_2$ to prepare 180 mL of a cell fluid ($1.1 \times 10^6$ cells/mL). For transfection, 250 µg of plasmid and 750 µg of PEI (polyethylenimine) were mixed with 20 mL of medium and then mixed with the prepared cell fluid. Then, the cells were incubated for 96 hours at 37° C. and 120 rpm in the presence of 8% $CO_2$ and then centrifuged (8,000 g, 10 minutes) to remove the cells and obtain the supernatant. The supernatant was mixed with phosphate buffer at pH 7.0 in a ratio of 1:1 and purified using proL agarose beads. Substances that failed to bind to the beads were removed by treatment with a phosphate buffer solution of pH 7.0. Single-chain antibody fragments were purified by treatment with a solution containing 0.1 M glycine at pH 2.5 to remove the bond between the single-chain antibody fragments and agarose beads, and then the pH was returned to a neutral range using 1 M pH 8.0 Tris buffer.

Figure 5:
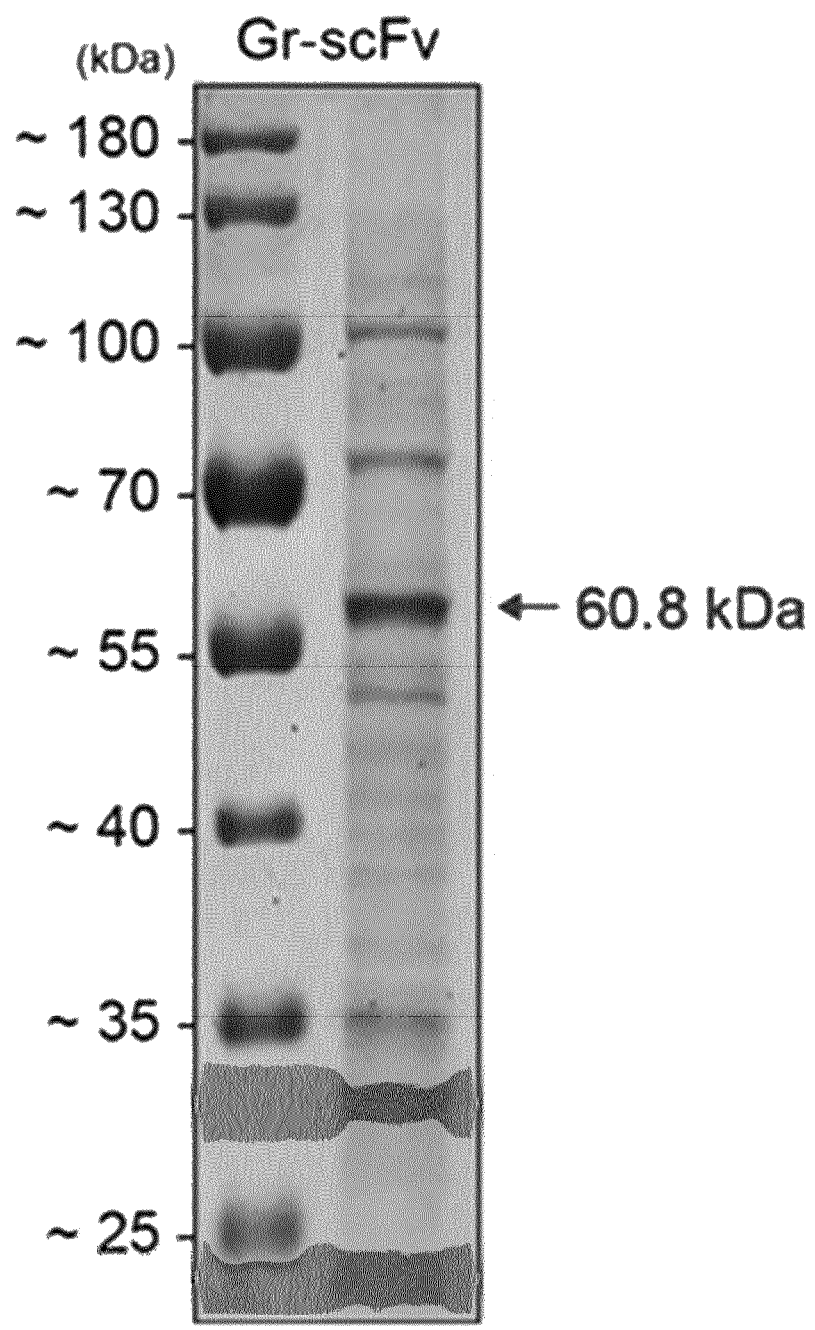
FIG. 5 shows the result of SDS gel electrophoresis to identify production of a single chain antibody fragment (grabber single chain variable fragment, Gr-scFv) of the present invention using a mammalian cell protein expression system.

Meanwhile, the purified single-chain antibody fragment was detected by SDS gel electrophoresis. The result showed that the single-chain antibody fragment for forming lipid nanoparticle of the present invention was produced intact (FIG. 5).

2-2. Production of Single Chain Antibody Fragment (Grabber Single Chain Variable Fragment-Fc, Gr-scFv-Fc) for Forming Lipid Nanoparticles In order to produce single chain antibody fragments (grabber single chain variable fragment-Fc, Gr-scFv-Fc) for forming lipid nanoparticles having the protein sequences of SEQ ID NOS. 10 to 18, the plasmid using the pcDNA3.1(+) vector produced in Example 1-2 was expressed using the mammalian cell expression system.

Specifically, HEK-293F (human embryonic kidney 293F) used as an expression host was incubated in an aqueous suspended cell state at 37° C. and 120 rpm in the presence of 8% $CO_2$ to prepare 180 mL of a cell fluid ($1.1 \times 10^6$ cells/mL). For transfection, 250 µg of plasmid and 750 µg of PEI (polyethylenimine) were mixed with 20 mL of medium and then mixed with the prepared cell fluid. Then, the cells were incubated for 96 hours at 37° C. and 120 rpm in the presence of 8% $CO_2$ and then centrifuged (8,000 g, 10 minutes) to remove the cells and obtain the supernatant. The supernatant was mixed with phosphate buffer at pH 7.0 in a ratio of 1:1 and purified using proL agarose beads. Substances that failed to bind to the beads were removed by treatment with a phosphate buffer solution of pH 7.0. Single-chain antibody fragments were purified by treatment with a solution containing 0.1 M glycine at pH 2.5 to remove the bond between the single-chain antibody fragments and agarose beads, and then the pH was returned to a neutral range using 1 M pH 8.0 Tris buffer.

Figure 6:
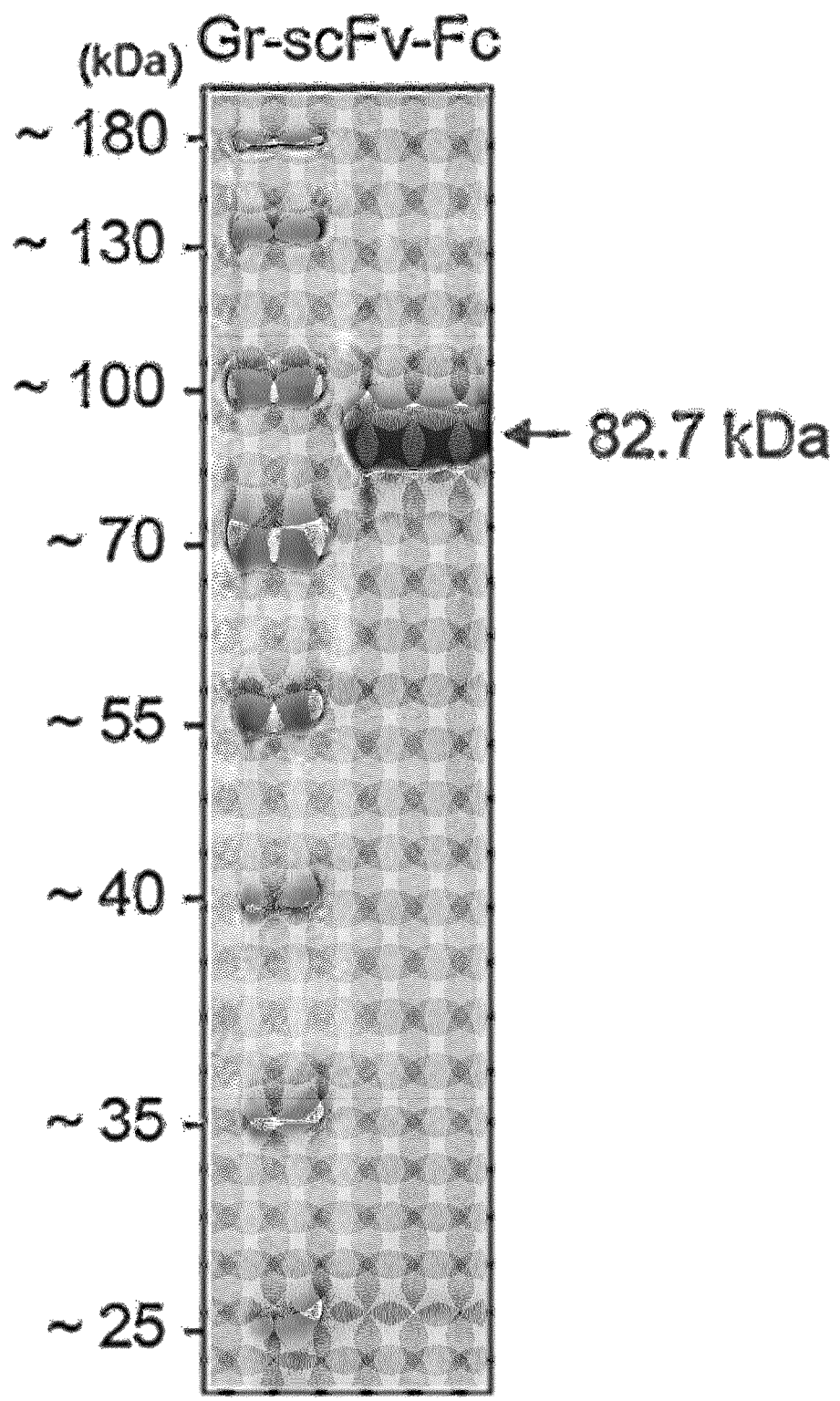
FIG. 6 shows the result of SDS gel electrophoresis to identify production of a single chain antibody fragment (grabber single chain variable fragment-Fc, Gr-scFv-Fc) of the present invention using mammalian cell protein expression system.

Meanwhile, the purified single-chain antibody fragment was detected by SDS gel electrophoresis. The result showed that the single-chain antibody fragment forming lipid nanoparticle of the present invention was produced intact (FIG. 6).

2-3. Production of Antibody (Gr-Antibody) for Forming Lipid Nanoparticles

In order to produce an antibody (Gr-antibody) for forming lipid nanoparticles having the IgL sequence of SEQ ID NOS. 19 to 21, and having the IgH sequence of SEQ ID NOS. 22 to 30, the plasmid using the pcDNA3.1(+) vector produced in Example 1-3 was expressed using the mammalian cell expression system.

Specifically, HEK-293F (human embryonic kidney 293F) used as an expression host was incubated in an aqueous suspended cell state at 37° C. and 120 rpm in the presence of 8% $CO_2$ to prepare 180 mL of a cell fluid ($1.1 \times 10^6$ cells/mL). For transfection, 250 µg of plasmid and 750 µg of PEI (polyethylenimine) were mixed with 20 mL of medium and then mixed with the prepared cell fluid. Then, the cells were incubated for 144 hours at 37° C. and 120 rpm in the presence of 8% $CO_2$ and then centrifuged (8,000 g, 10 minutes) to remove the cells and obtain the supernatant. The supernatant was mixed with phosphate buffer at pH 7.0 in a ratio of 1:1 and purified using proL agarose beads. Substances that failed to bind to the beads were removed by treatment with a phosphate buffer solution of pH 7.0. The antibody was purified by treating a solution containing 0.1 M glycine at pH 2.5 to remove the bond between the antibody fragments and agarose beads, and then pH was returned to a neutral range using 1 M pH 8.0 Tris buffer.

Meanwhile, the purified antibody was detected by SDS gel electrophoresis. The result showed that the antibody for forming lipid nanoparticles of the present invention was produced intact (FIG. 7).

Figure 7:
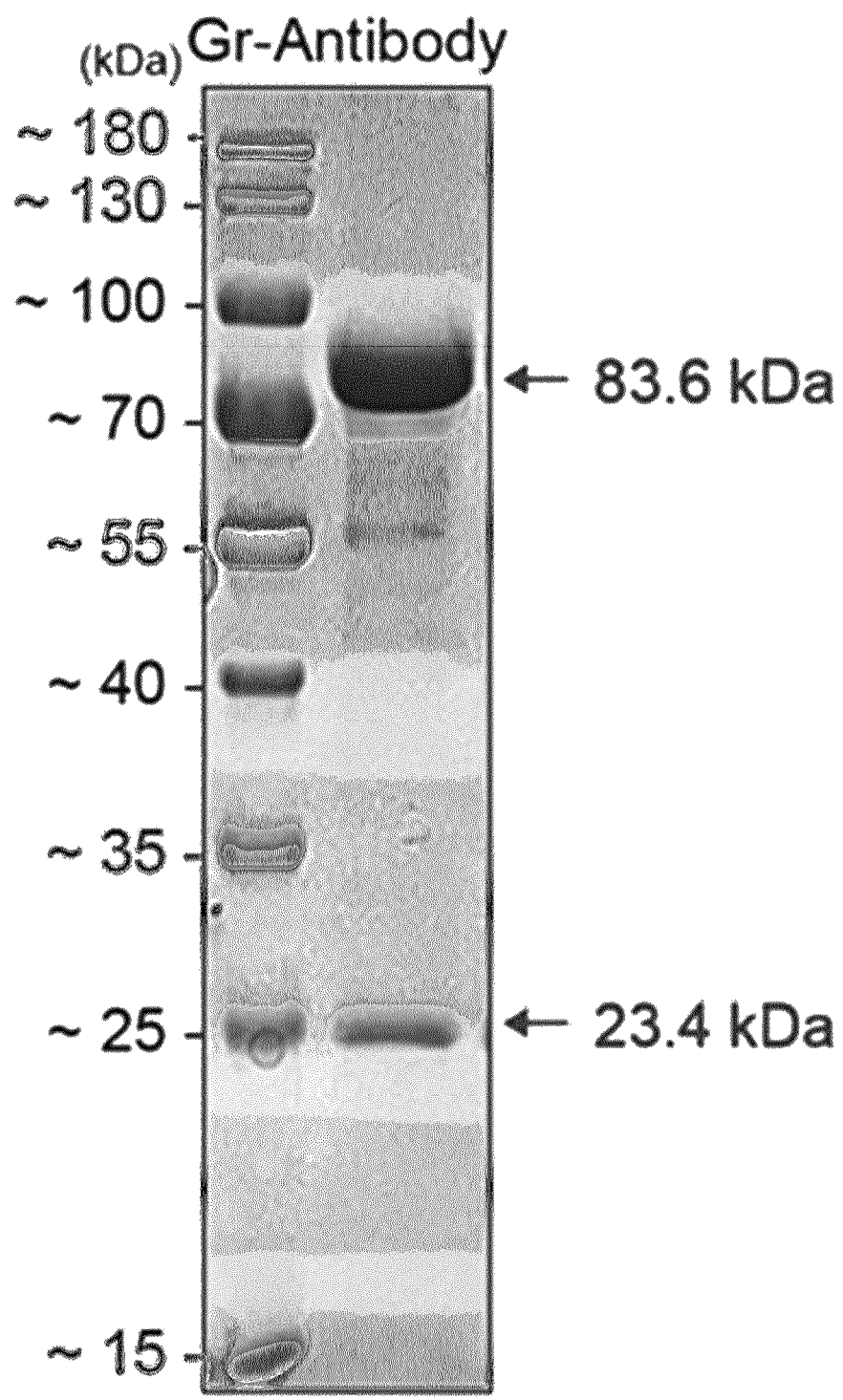
FIG. 7 shows the result of SDS gel electrophoresis to identify production of an antibody (grabber antibody, Gr-antibody) of the present invention using a mammalian cell protein expression system.

Meanwhile, in FIG. 7, 83.6 kDa represents a protein consisting of a variable region of heavy chain (VH), a constant region of heavy chain (CH), and apolipoprotein, and 23.4 kDa represents a protein consisting of a variable region of light chain (VL) and a constant region of light chain (CL).

Example 3: Confirmation of Adhesion of Membrane Scaffold Protein to Lipid Nanoparticles In this example, the adhesion of membrane scaffold proteins to lipid nanoparticles was detected to determine whether or not membrane scaffold proteins could attach to antibody-bound lipid nanoparticles by mixing the antibody for forming lipid nanoparticles of the present invention with lipid nanoparticles.

3-1. Production of Lipid Nanoparticles

SM102 (CAS No. 2089251-47-6), DSPC (1,2-distearoyl-sn-glycero-3-phosphocholine), cholesterol, and DMG-PEG-2000 (1,2-dimyristoyl-rac-glycero-3-methoxypolyethylene glycol-2000) were dissolved in ethanol to prepare a lipid solution. Meanwhile, 75 L of messenger ribonucleic acid (messenger RNA, mRNA) was mixed with aqueous phase mRNA buffer (10.25 mM citric acid, 2.25 mM tri-sodium citrate, pH 3.0) to prepare an RNA solution. The lipid solution and the RNA solution prepared above were mixed using a microfluidic device such that the molar ratio of SM102:DSPC:cholesterol:DMG-PEG-2000 was 50:10:38.5:1.5, and the molar ratio of the amino group of SM102, which is an ionized lipid, to the phosphate group of mRNA (N/P ratio) was 6. Then, PBS was added to the mixture and diluted to a 4-fold volume ratio to prepare a lipid nanoparticle solution.

3-2. Confirmation of Adhesion of Membrane Scaffold Proteins to Lipid Nanoparticles MSP1E3D1 derived from apolipoprotein AI as a membrane scaffold protein was mixed with the lipid nanoparticle solution prepared in 3-1 above at a molar ratio of lipid to protein (LP ratio) of 240:1, and incubated at 4° C. for 16 hours to attach membrane scaffold proteins to lipid nanoparticles.

Figure 8:
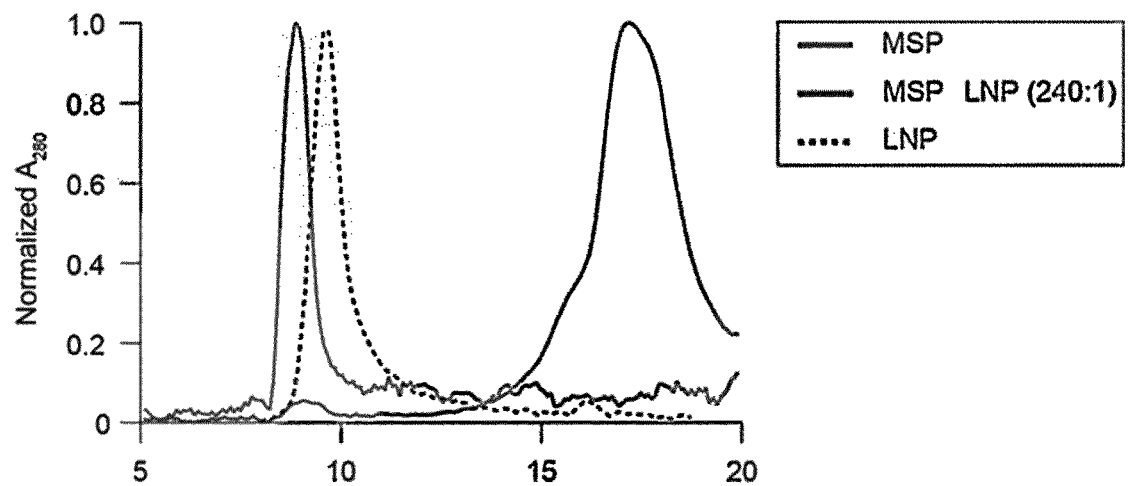
FIG. 8 shows $A_{280}$ of a membrane scaffold protein (MSP), a lipid nanoparticle (LNP), and a mixture (MSP LNP) of the lipid nanoparticle and the membrane scaffold protein (MSP) measured through size exclusion chromatography in order to determine whether or not the antibody of the present invention can bind to the lipid nanoparticle.

Then, $A_{280}$ of lipid nanoparticles (LNP), membrane scaffold protein (MSP), and membrane scaffold protein-attached lipid nanoparticles (MSP-LNP) were determined through size exclusion chromatography (FIG. 8).

As can be seen from FIG. 8, the $A_{280}$ peak shifts when lipid nanoparticles (LNP) are mixed with the membrane scaffold protein (MSP), which means that the membrane scaffold protein (MSP) is intactly attached to the lipid nanoparticle (LNP).

Figure 9:
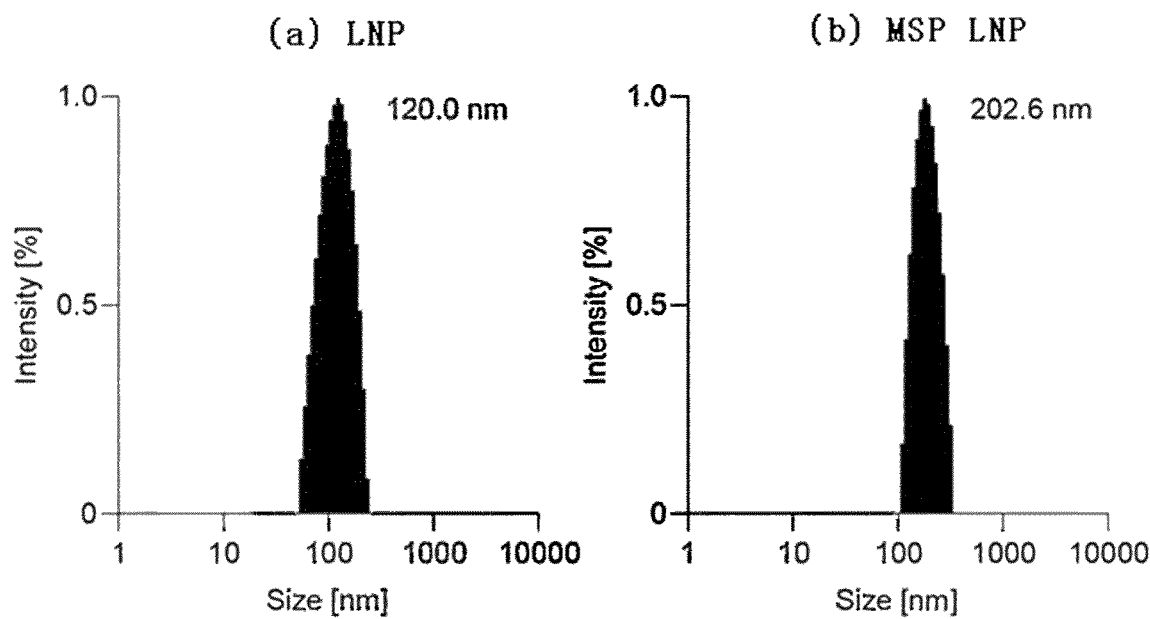
FIG. 9 shows the particle size of a lipid nanoparticle (LNP), and a mixture (MSP LNP) of the lipid nanoparticle and a membrane scaffold protein measured through dynamic light scattering in order to determine whether or not the antibody of the present invention can bind to the lipid nanoparticle.

In addition, the particle sizes of the lipid nanoparticle (LNP) and the membrane scaffold protein-attached lipid nanoparticle (MSP-LNP) were measured using dynamic light scattering (FIG. 9).

As can be seen from FIG. 9, the membrane scaffold protein-attached lipid nanoparticle has a large particle size, which indicates that the membrane scaffold protein (MSP) is intactly attached to the lipid nanoparticle (LNP).

The results mean that the antibody for forming the lipid nanoparticle of the present invention containing the membrane scaffold protein has excellent adhesion to the lipid nanoparticle.

Example 4: Production of Antibody-Bound Lipid Nanoparticles of the Present Invention Using Antibodies for Forming Lipid Nanoparticles In this example, antibody-bound lipid nanoparticles were produced using the single-chain antibody for forming the lipid nanoparticles of the present invention produced in Example 2-2.

In addition, the lipid nanoparticles and the single chain antibody for forming the lipid nanoparticles of the present invention were produced at different mixing times and different mixing ratios, and the optimized mixing time and ratio were selected.

4-1. Selection of Mixing Time of Lipid Nanoparticles and Single Chain Antibodies for Forming Lipid Nanoparticles of the Present Invention SM102 (CAS No. 2089251-47-6), DSPC (1,2-distearoyl-sn-glycero-3-phosphocholine), cholesterol, and DMG-PEG-2000 (1,2-dimyristoyl-rac-glycero-3-methoxypolyethylene glycol-2000) were dissolved in ethanol to prepare a lipid solution. Meanwhile, 75 µL of messenger ribonucleic acid (messenger RNA, mRNA) was mixed with aqueous phase mRNA buffer (10.25 mM citric acid, 2.25 mM tri-sodium citrate, pH 3.0) to prepare an RNA solution. The lipid solution and the RNA solution prepared above were mixed using a microfluidic device such that the molar ratio of SM102:DSPC:cholesterol:DMG-PEG-2000 was adjusted to 50:10:38.5:1.5, and the molar ratio of the amino group of SM102, which is an ionized lipid, to the phosphate group of mRNA (N/P ratio) was adjusted to 6. Then, the mixture was diluted to a 4-fold volume ratio using PBS to form lipid nanoparticles. At this time, the dilution was performed three times, a single chain antibody for forming the lipid nanoparticles of the present invention was added thereto such that a molar ratio of the lipid to protein (LP ratio) was adjusted to 240:1, and reacted at 37° C. for 1 hour to form antibody-bound lipid nanoparticles.

At this time, the experimental group to which the single-chain antibody for forming the lipid nanoparticles of the present invention was added during the first dilution was referred to as "early", the experimental group to which the single-chain antibody for forming the lipid nanoparticles of the present invention was added during the second dilution was referred to as "middle", the experimental group to which the single-chain antibody for forming the lipid nanoparticles of the present invention was added during the third dilution was referred to as "late", and the experimental group to which the single-chain antibody for forming the lipid nanoparticles of the present invention was added in uniform portions during a total of 3 dilutions was referred to as "total".

Then, a RiboGreen assay was performed to determine whether or not the antibody-bound lipid nanoparticles of the present invention were successfully formed.

Specifically, 20 µL of each of lipid nanoparticles and antibody-bound lipid nanoparticles were diluted in 180 µL of dPBS. The dilution was further mixed with 200 µL of dPBS or 1% Triton X-100 in dPBS, followed by reaction for 10 minutes to prepare a dilute solution of lipid nanoparticles and a dilute solution of antibody-bound lipid nanoparticles. 100 µL of the RNA solution in the standard concentration range (dPBS standard and 0.5% Triton X-100 in dPBS standard), 100 μL of the prepared lipid nanoparticle dilution solution and 100 μL of the prepared antibody-bound lipid nanoparticle dilution solution were added to a 96 well plate and reacted at 25° C. for 5 minutes. Then, excitation/emission=485/530 nm was measured using a fluorescence spectrophotometer to determine the mRNA concentration (FIG. 10).

Meanwhile, in FIG. 10, the mRNA concentration of the experimental group diluted using dPBS is shown as a concentration of unencapsulated free mRNA, and the mRNA concentration of the experimental group diluted with 1% Triton X-100 in dPBS is shown as the total mRNA concentration. Encapsulation was calculated as (1−(free mRNA/total mRNA))×100%.

This indicates that antibody-bound lipid nanoparticles were formed intact even when mixed with single-chain antibodies for forming the lipid nanoparticles of the present invention while the lipid nanoparticles were formed. In addition, this indicates that the encapsulation of mRNA increases as the single chain antibody for forming the lipid nanoparticles of the present invention was added later. Therefore, in the following experiment, the antibody-bound lipid nanoparticles of the present invention were produced by adding the single-chain antibody for forming the lipid nanoparticles of the present invention after the lipid nanoparticles were formed intact.

4-2. Selection of Mixing Ratio of Lipid Nanoparticles and Single Chain Antibodies for Forming Lipid Nanoparticles of the Present Invention SM102 (CAS No. 2089251-47-6), DSPC (1,2-distearoyl-sn-glycero-3-phosphocholine), cholesterol, and DMG-PEG-2000 (1,2-dimyristoyl-rac-glycero-3-methoxypolyethylene glycol-2000) were dissolved in ethanol to prepare a lipid solution. Meanwhile, 75 μL of messenger ribonucleic acid (messenger RNA, mRNA) was mixed with aqueous phase mRNA buffer (10.25 mM citric acid, 2.25 mM tri-sodium citrate, pH 3.0) to prepare an RNA solution. The lipid solution and the RNA solution prepared above were mixed using a microfluidic device such that the molar ratio of SM102:DSPC:cholesterol:DMG-PEG-2000 was 50:10:38.5:1.5, and the molar ratio of the amino group of SM102, which is an ionized lipid, to the phosphate group of mRNA (N/P ratio) was 6. The mixture was diluted 4 times by volume using PBS to form lipid nanoparticles. Single-chain antibodies for forming the lipid nanoparticles of the present invention were added to the lipid nanoparticles at various lipid:protein molar ratios (LP ratio), and reacted at 4° C. for 16 hours to form antibody-bound lipid nanoparticles.

Figure 11:
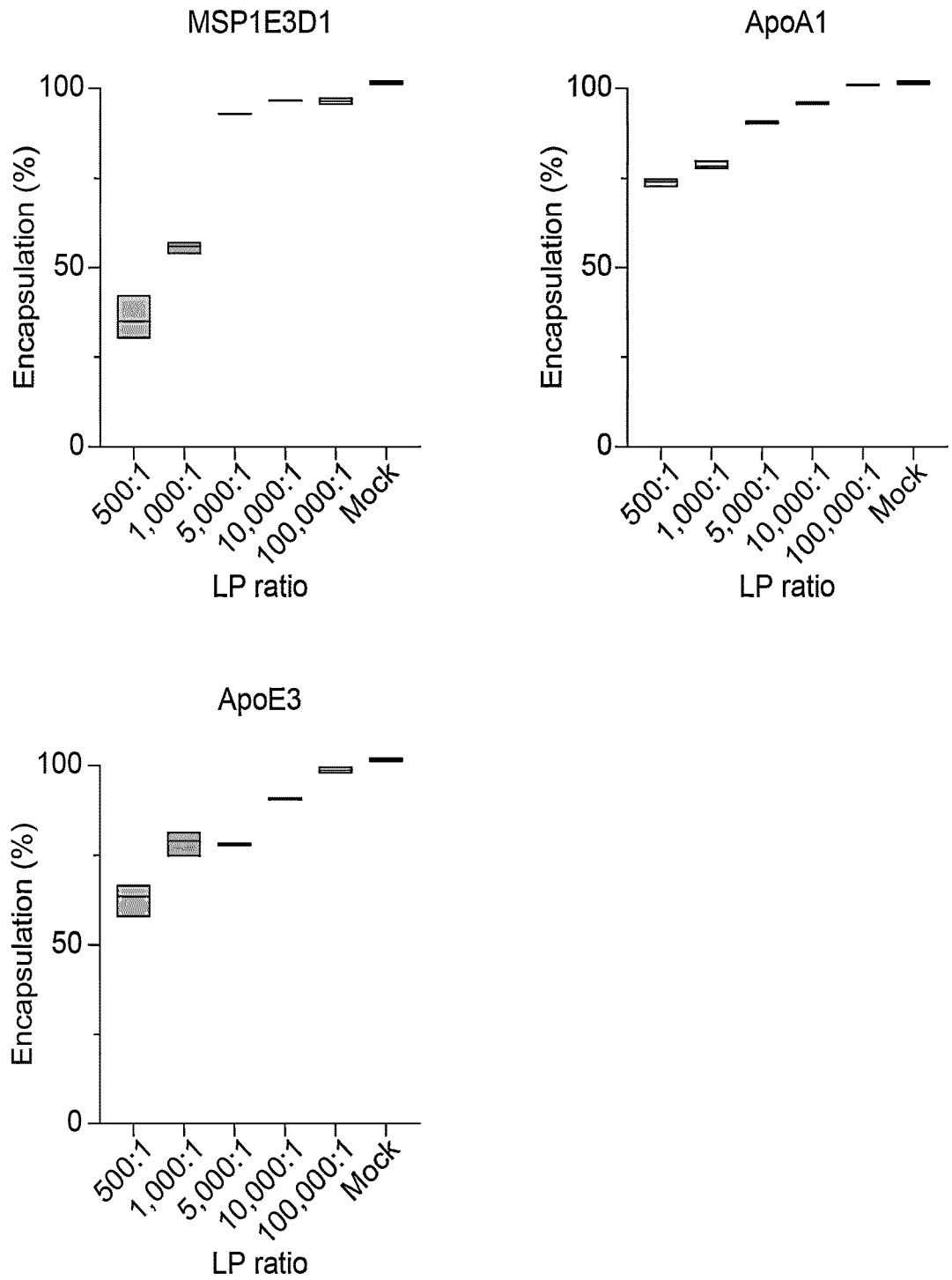
FIG. 11 shows the mRNA encapsulation (%) of antibody-bound lipid nanoparticles produced by mixing the antibody with lipid nanoparticles at different molar ratios (LP ratios) of the lipid to protein, in order to optimize the mixing time of the lipid nanoparticle with the antibody of the present invention.
Figure 12:
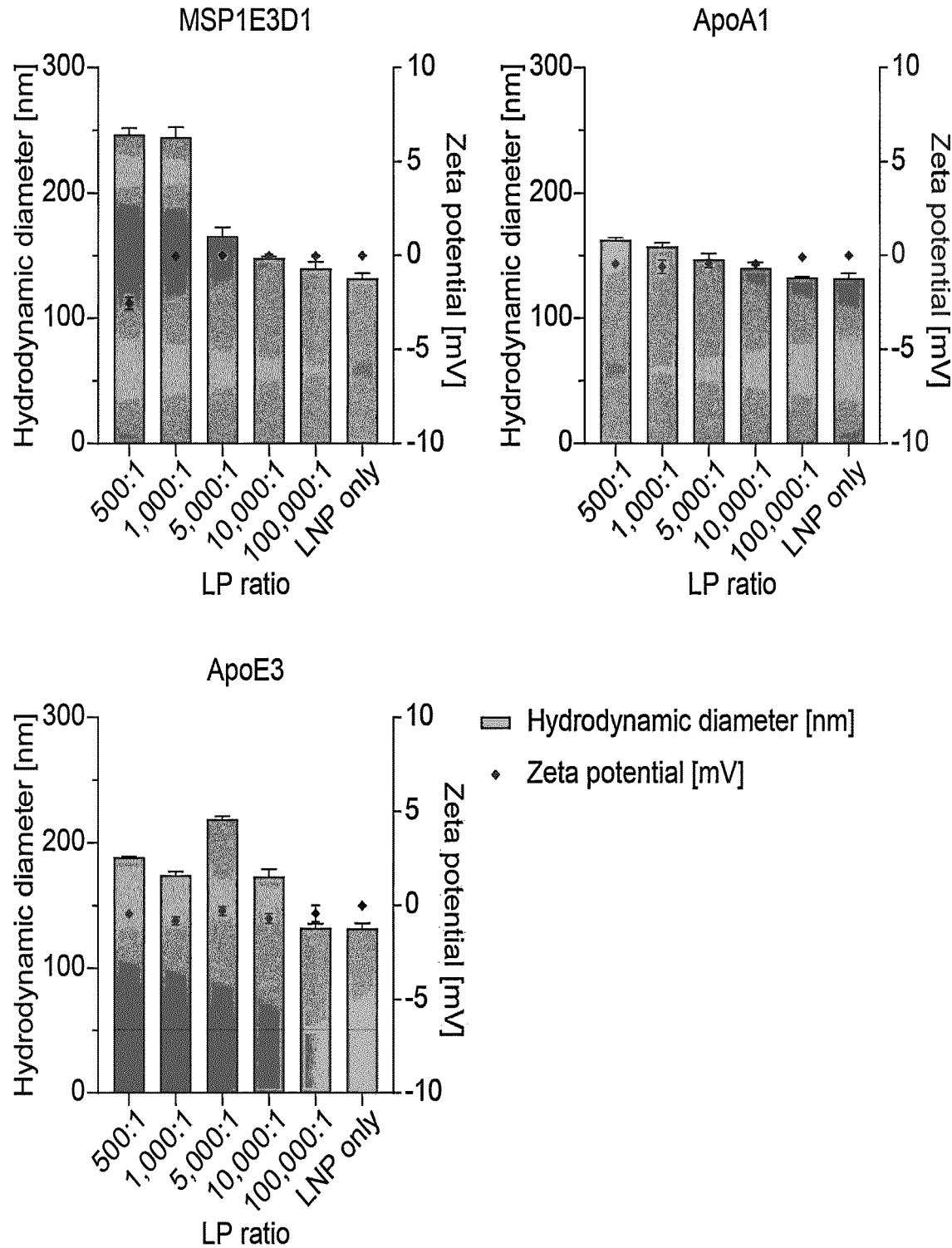
FIG. 12 shows the particle sizes of antibody-bound lipid nanoparticles, which are produced by mixing the antibody with lipid nanoparticles at different molar ratios (LP ratios) of the lipid to protein, measured through dynamic light scattering, in order to optimize the mixing time of the lipid nanoparticle with the antibody of the present invention.

Then, the encapsulation was calculated by performing Ribogreen assay in the same manner as in Example 4-1 (FIG. 11) and the size of the formed antibody-bound lipid nanoparticles of the present invention was measured by performing dynamic light scattering in the same manner as in Example 3-2 (FIG. 12).

The results showed that the encapsulation was as high as about 95% at an LP ratio of 5,000:1 to 100,000:1, and that the size was increased because the single chain antibody for forming the lipid nanoparticles of the present invention was attached to the lipid nanoparticles.

Example 5: Confirmation of Storage Stability of Antibody-Bound Lipid Nanoparticles of the Present Invention In this example, the storage stability of the antibody-bound lipid nanoparticles of the present invention was determined.

5-1. Changes in mRNA Encapsulation of Antibody-Bound Lipid Nanoparticles Depending on Storage Time The antibody-bound lipid nanoparticle of the present invention containing Firefly luciferase mRNA, a fragment of the NLDC145 antibody that binds to the ligand of MutuDC1940, and a membrane scaffold protein (MSP1E3D1, ApoA1 or ApoE3) was produced using the method of Example 4-2. Then, changes in mRNA encapsulation were observed while the antibody-bound lipid nanoparticle was stored at 4° C. On the day at which the antibody-bound lipid nanoparticle was formed and 7 days later, Ribogreen assay was performed in the same manner as in Example 4-1 to calculate the encapsulation (FIG. 13).

Figure 13:
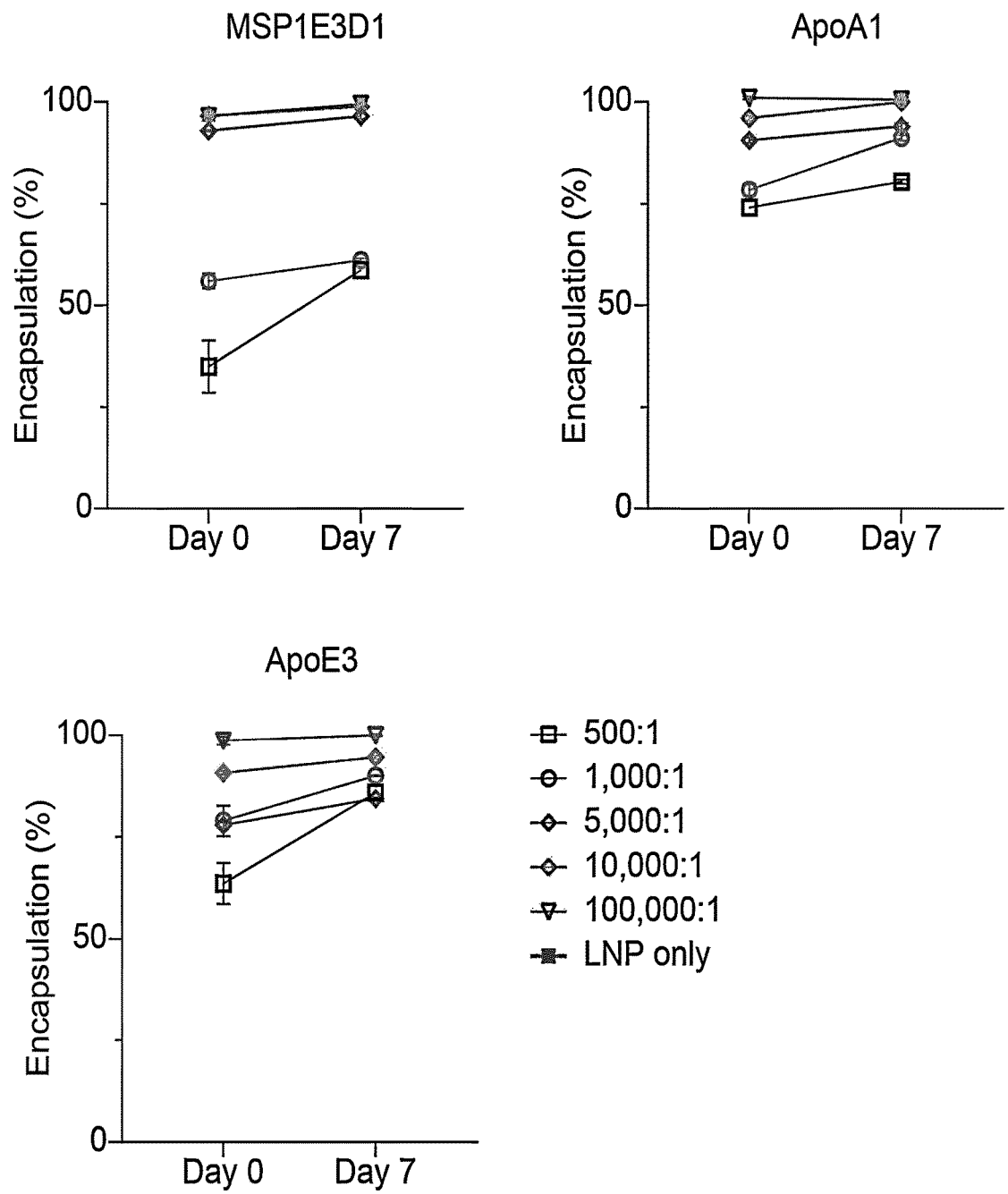
FIG. 13 shows changes in encapsulation observed while the antibody-bound lipid nanoparticles of the present invention are stored at 4° C. for 7 days to determine the storage stability of the antibody-bound lipid nanoparticles.

As can be seen from FIG. 13, the mRNA encapsulation of the antibody-bound lipid nanoparticles of the present invention does not decrease even 7 days after production. The results mean that mRNA is not released from the lipid nanoparticles even when the antibody for forming the lipid nanoparticles of the present invention was attached to the lipid nanoparticles.

Figure 14:
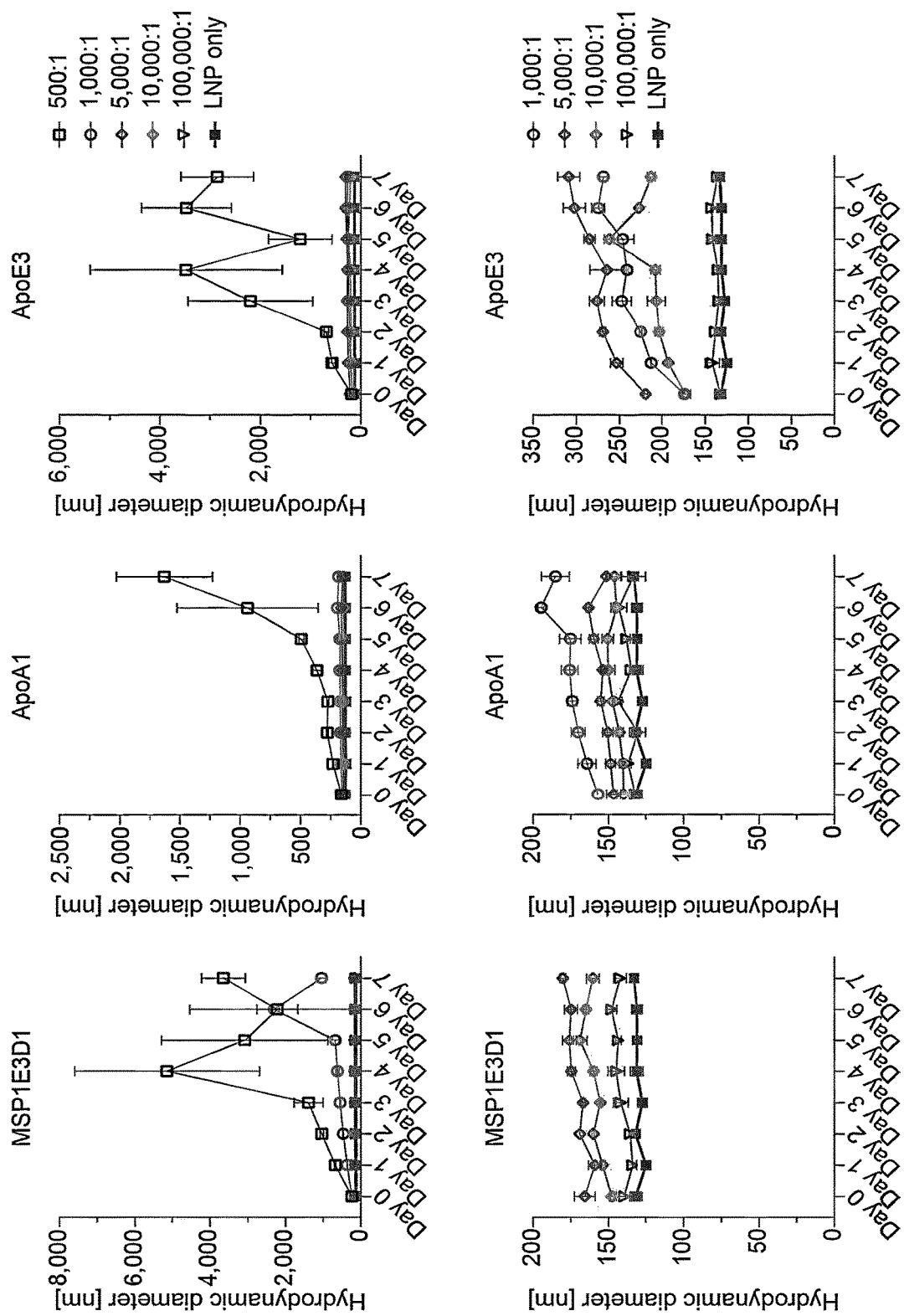
FIG. 14 shows the size of the antibody-bound lipid nanoparticles of the present invention observed while the antibody-bound lipid nanoparticles are stored at 4° C. for 7 days to determine the storage stability of the antibody-bound lipid nanoparticles.

5-2. Size Change of Antibody-Bound Lipid Nanoparticles Depending on Storage Time The antibody-bound lipid nanoparticles of the present invention produced in Example 5-1 were stored at 4° C. and dynamic light scattering was performed in the same manner as in Example 3-2 to determine the size change of the antibody-bound lipid nanoparticles for 7 days (FIG. 14). Meanwhile, in FIG. 14, the top and the bottom diagrams show the same experimental results wherein the top diagram shows the result including the experimental group with an LP ratio of 500:1, and the bottom diagram shows the result excluding the experimental group with an LP ratio of 500:1.

As can be seen from FIG. 14, the antibody-bound lipid nanoparticles of the present invention maintain a constant size over time when the LP ratio is greater than 5,000:1, but the size increases dramatically when the LP ratio is 500:1 to 1,000:1. This indicates that stable antibody-bound lipid nanoparticles were formed only when the LP ratio exceeded 5,000:1.

Example 6: Confirmation of Binding Ability of Antibody-Bound Lipid Nanoparticles of the Present Invention to Target Cells In this example, whether or not the antibody-bound lipid nanoparticles of the present invention specifically bind to target cells was determined.

The antibody-bound lipid nanoparticles of the present invention were produced in the same manner as in Example 5-1, except that DiD (DiIC18 (5); 1,1'-dioctadecyl-3,3,3',3'-tetramethylindodicarbocyanine, 4-chlorobenzenesulfonate salt) dye was added at a molar ratio of 1% of the lipid to produce DID-antibody-bound lipid nanoparticles.

A549 cells grown using RPMI-1640 medium and MutuDC1940 cells grown in IMDM medium supplemented with 10 mM HEPES and 50 μM β-mercaptoethanol were prepared. Meanwhile, the A549 cells were used as an experimental group that did not express the target ligand and the MutuDC1940 cells were used as an experimental group that constantly expressed the target ligand.

100 μL of the A549 cells were seeded at a concentration of $1.5 \times 10^5$ cells/mL per well in a 96 well black plate. The MutuDC1940 cells were coated with collagen I at a concentration of 50 μg/mL to ensure efficient attachment to the plate, and then 100 μL of MutuDC1940 cells were seeded at a concentration of $3.5 \times 10^5$ cells/mL per well. The cells were incubated for one day to ensure efficient attachment to the plate and then were treated with the antibody-bound lipid nanoparticles of the present invention such that the final lipid concentration was adjusted to 10 μg/mL. The cells were incubated at 37° C. in the presence of 5% $CO_2$ for 30 minutes and then the supernatant was removed. The cells were washed twice with PBS (phosphate buffered saline) and then treated with 100 μL of cell lysis buffer at 37° C. for 5 minutes to lyse the cells. Then, fluorescence was measured at Ex/Em=644/663 nm using a plate reader to confirm the relative binding ability of the antibody-bound lipid nanoparticles of the present invention (FIG. 15).

Figure 15:
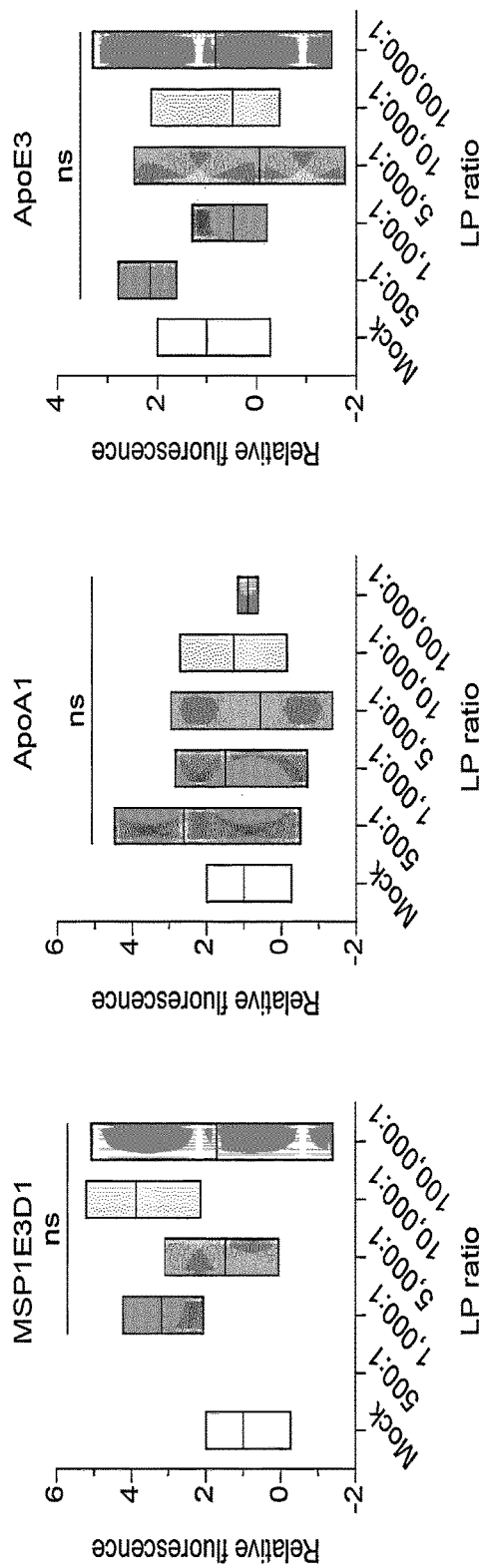
FIG. 15 shows fluorescence measured to determine relative binding ability after treating MutuDC1940 cells expressing the target ligand and A549 cells not expressing the target ligand with antibody-bound lipid nanoparticles containing DiD dye, in order to determine whether or not the antibody-bound lipid nanoparticles of the present invention specifically bind to the target cells.
Figure 15:
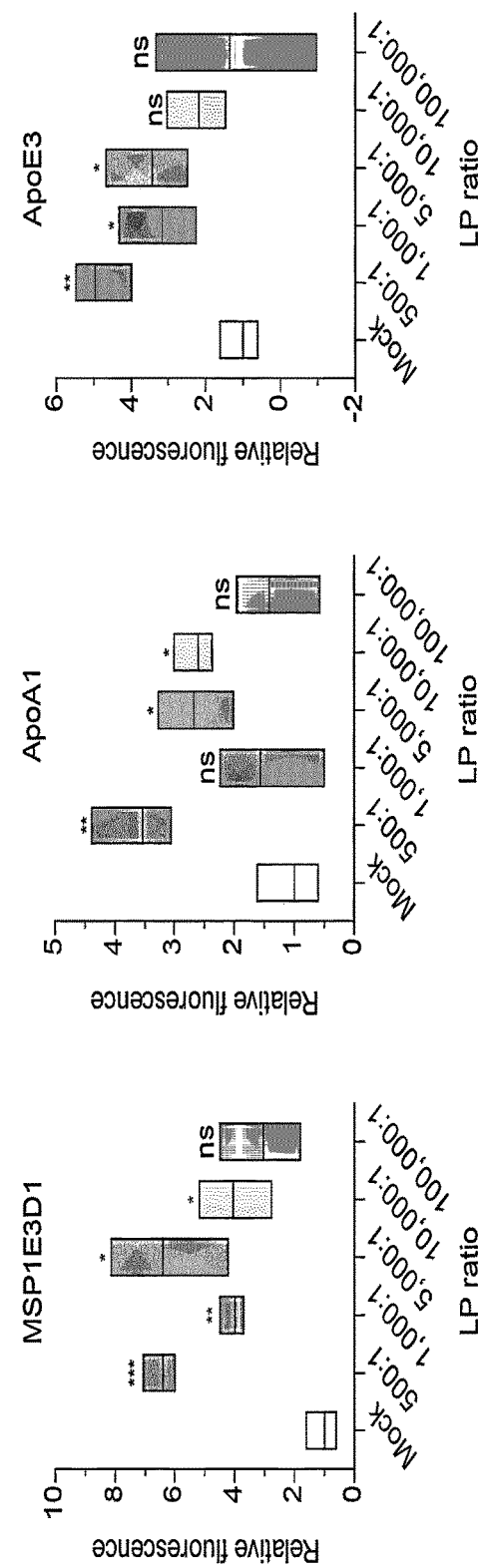

As can be seen from FIG. 15, in the experimental group treated with A549 cells not expressing the target ligand, there is no difference between the antibody-bound lipid nanoparticles of the present invention and general lipid nanoparticles, whereas, in the experimental group treated with MutuDC1940 cells expressing the target ligand, the antibody-bound lipid nanoparticles of the present invention exhibit higher fluorescence values. The results mean that the antibody-bound lipid nanoparticles of the present invention can bind better and specifically to target cells expressing the target ligand.

Example 7: Confirmation of mRNA Delivery Ability of Antibody-Bound Lipid Nanoparticles of the Present Invention In this example, whether or not the antibody-bound lipid nanoparticles of the present invention specifically deliver captured mRNA to target cells was determined.

7-1. Confirmation of mRNA Delivery in the Absence of Serum

A luciferase assay was performed to determine whether or not the antibody-bound lipid nanoparticles of the present invention produced in Example 5-1 successfully delivered mRNA to target cells.

A549 cells grown in RPMI-1640 medium and MutuDC1940 cells grown in IMDM medium supplemented with 10m M HEPES and 50 μM β-mercaptoethanol were prepared. Meanwhile, the A549 cells were used as an experimental group in which serum is absent and the target ligand is not expressed, and the MutuDC1940 cells were used as an experimental group in which serum is present and the target ligand is expressed.

500 μL of the A549 cells were seeded in a 96 well black plate at a concentration of $2 \times 10^5$ cells/mL per well. The MutuDC1940 cells were coated with collagen I at a concentration of 50 μg/mL to ensure efficient attachment to the plate, and then 500 μL of MutuDC1940 cells were seeded at a concentration of $4 \times 10^5$ cells/mL per well. The cells were incubated for one day to ensure efficient adhesion to the plate and then were treated with the antibody-bound lipid nanoparticles of the present invention at 125 ng of total mRNA per well. The cells were incubated for 12 hours at 37° C. in the presence of 5% $CO_2$ and then the supernatant was removed. The cells were treated with 200 μL of cell lysis buffer at 37° C. for 5 minutes to lyse the cells, and then 100 μL of the supernatant was transferred to a white 96 well plate. After adding 50 μL of luciferase substrate, luminescence was measured using a plate reader and the relative expression level of the Firefly luciferase gene was determined based on the experimental group treated with general lipid nanoparticles (FIG. 16).

Figure 16:
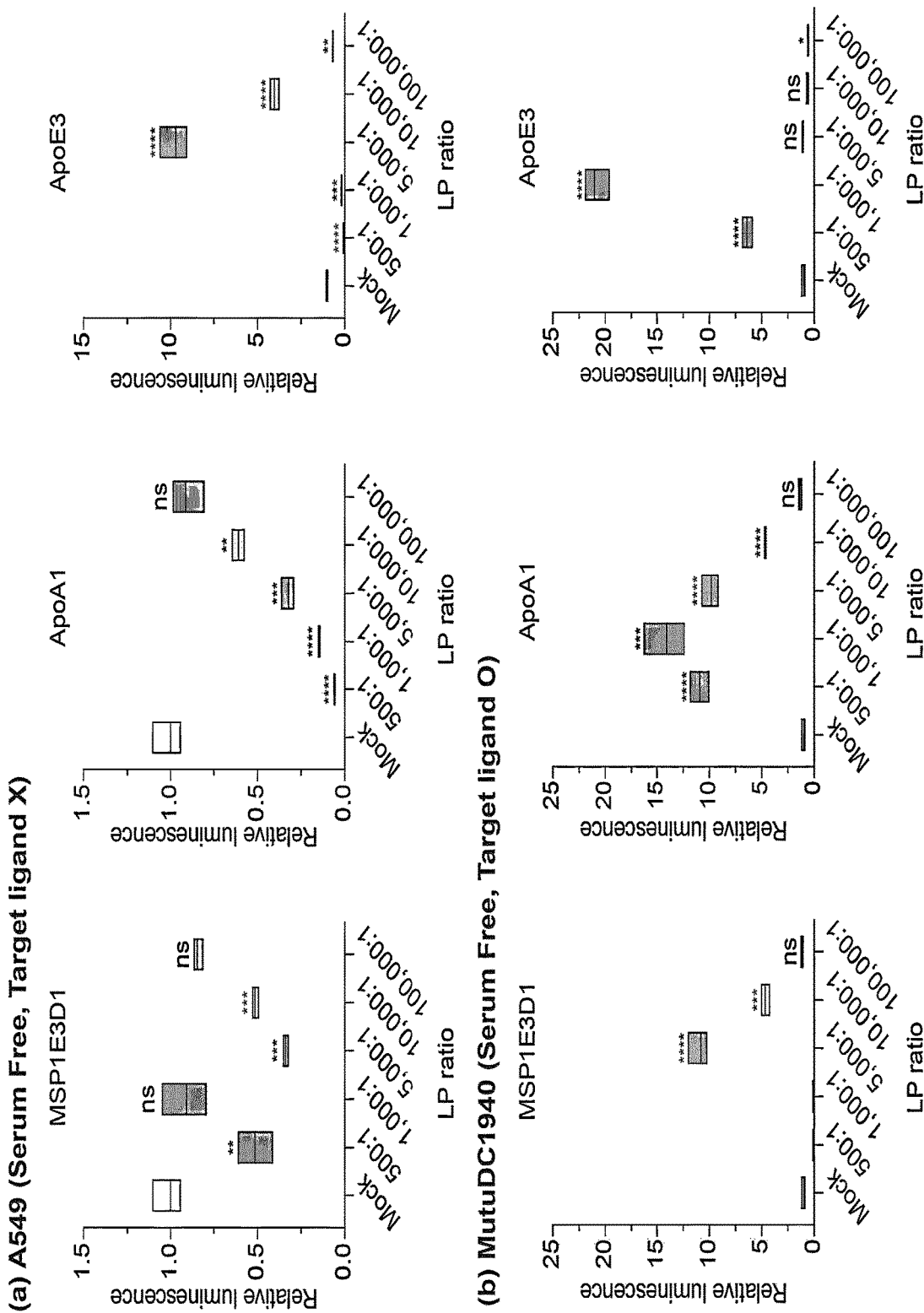
FIG. 16 shows relative gene expression levels in cells measured after treating MutuDC1940 cells expressing the target ligand and A549 cells not expressing the target ligand with antibody-bound lipid nanoparticles, in order to determine whether or not the antibody-bound lipid nanoparticles of the present invention deliver mRNA specifically to the target cells.

As can be seen from FIG. 16, in the experimental group treated with A549 cells that did not express the target ligand, the antibody-bound lipid nanoparticles of the present invention had a lower gene expression level than general lipid nanoparticles in most cases. In addition, it can be seen that, as the amount of the antibody of the present invention decreases, the expression level in cells that did not express the target ligand increases.

On the other hand, in the experimental group treated with MutuDC1940 cells expressing the target ligand, the expression level increased approximately 5 to 20 times at the LP ratio of 5,000:1 to 10,000:1 for MSP1E3D1, at the LP ratio of 500:1 to 10,000:1 for ApoA1, and at the LP ratio of 500:1 to 1,000:1 for ApoE3.

The results indicate that the antibody-bound lipid nanoparticle of the present invention exhibits more specific delivery ability than general antibody-bound lipid nanoparticles, because general lipid nanoparticles delivered randomly the contained mRNA, but the antibody-bound lipid nanoparticle of the present invention contains membrane scaffold proteins to suppress the delivery of mRNA to random cells, and contains an antibody to improve the delivery of mRNA to cells.

7-2. Confirmation of mRNA Delivery in the Presence of Serum

Whether or not the antibody-bound lipid nanoparticles of the present invention successfully delivered mRNA to target cells, like in Example 7-1, was determined even in the presence of serum without an influence from serum.

For this purpose, luciferase assay was performed in the same manner as in 5-1 to determine gene expression levels, except that A549 cells grown in RPMI-1640 medium supplemented with 10% FBS and MutuDC1940 cells grown in IMDM medium supplemented with 10% FBS, 10 mM HEPES, and 50 UM β-mercaptoethanol were used.

Figure 17:
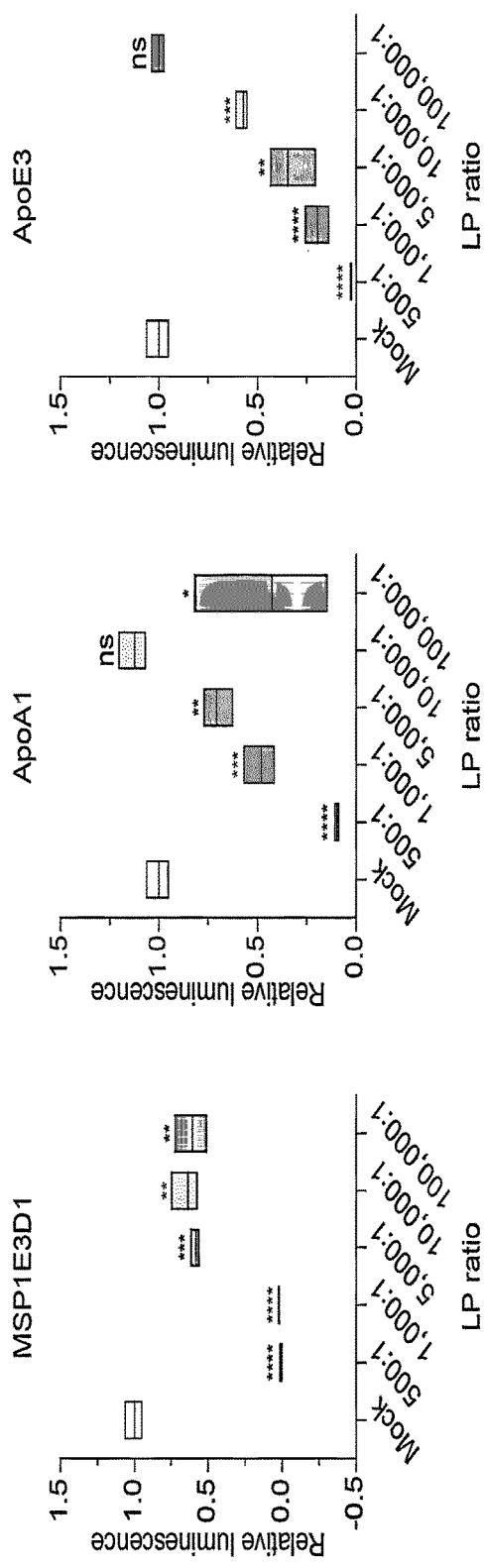
FIG. 17 shows relative gene expression levels in cells measured after treating MutuDC1940 cells expressing the target ligand and A549 cells not expressing the target ligand in the presence of a serum with antibody-bound lipid nanoparticles, in order to determine whether or not the antibody-bound lipid nanoparticles of the present invention deliver mRNA specifically to the target cells even if they are hindered by serum.
Figure 17:
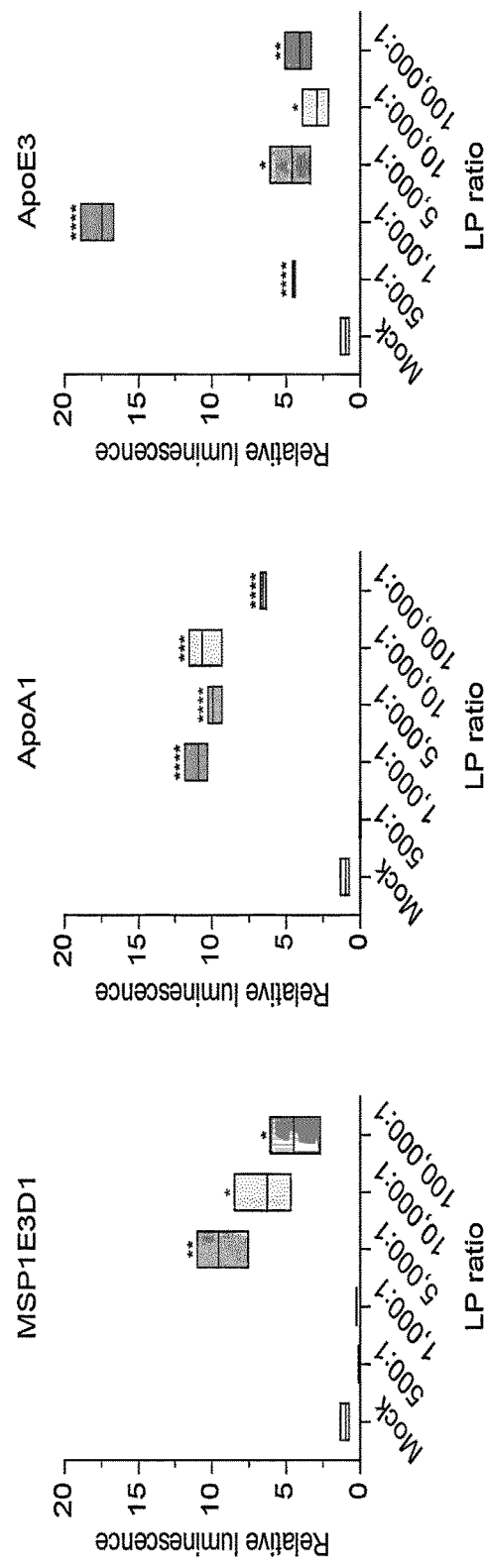

As can be seen from FIG. 17, in the experimental group treated with A549 cells that did not express the target ligand, the antibody-bound lipid nanoparticle of the present invention had a lower gene expression level than general lipid nanoparticles in most cases.

On the other hand, in the group containing the scFv (NLDC145) of the antibody when treated with MutuDC1940 cells expressing the target ligand, the expression level increased approximately 5 to 20 times at a ratio of 5,000:1 to 100,000:1 for MSP1E3D1, at a ratio of 1,000:1~100,000:1 for ApoA1, and a ratio of 500:1 to 100,000:1 for ApoE3.

The results show that, even in the presence of serum such as bodily fluids, the antibody-bound lipid nanoparticle of the present invention exhibits more specific delivery ability than general antibody-bound lipid nanoparticles, because general lipid nanoparticles delivered the contained mRNA randomly without cell specificity, but the antibody-bound lipid nanoparticle of the present invention contains membrane scaffold proteins to suppress the delivery of mRNA to random cells, and contains an antibody to improve the delivery of mRNA to cells.

The invention claimed is:

1. An antibody-bound lipid nanoparticle in which an antibody or antibody fragment is conjugated to a lipid nanoparticle via an amphipathic membrane scaffold protein having a helix structure, wherein the membrane scaffold protein is spread across a surface of the lipid nanoparticle, and a shape of the membrane scaffold protein is such that one side of the membrane scaffold protein faces a hydrophobic interior region of a lipid monolayer of the lipid nanoparticle, and the other side of the membrane scaffold protein faces a hydrophilic exterior of the lipid monolayer of the lipid nanoparticle.

2. The antibody-bound lipid nanoparticle according to claim 1, wherein the antibody fragment is scFv or scFV-Fc.

3. The antibody-bound lipid nanoparticle according to claim 1, wherein the antibody or antibody fragment conjugated with the membrane scaffold protein is produced by binding a gene encoding the antibody or antibody fragment to a gene encoding the membrane scaffold protein and expressing the result.

4. The antibody-bound lipid nanoparticle according to claim 1, wherein the lipid nanoparticle comprises a substance encapsulated therein.

5. The antibody-bound lipid nanoparticle according to claim 4, wherein the encapsulated substance is nucleic acid.

* * * * *

SEQUENCE LISTING

Sequence total quantity: 30
SEQ ID NO: 1          moltype = AA   length = 525

```
FEATURE                   Location/Qualifiers
source                    1..525
                          mol_type = protein
                          organism = synthetic construct
SEQUENCE: 1
MAVQIVESGG GLVQPKESLK ISCTASGFTF SNAAIYWVRQ TPGKGLEWVG RIRTRPSKYA   60
TDYADSVRGR FTISRDDSKS MVYLQMDNLR TEDTAMYYCT PRATEDVPFY WGQGVMVTVS  120
SGGGGSGGGG SGGGGSDIVM TQTPSSQAVS AGEKVTMNCK SSQSVLYDEN KKNYLAWYQQ  180
KSGQSPKLLI YWASTGESGV PDRFIGSGSG TDFTLTISSV QAEDLAVYYC QQYYDFPPTF  240
GGGGTKLELKA SGGGGSGGGG STFSKLREQL GPVTQEFWDN LEKETEGLRQ EMSKDLEEVK  300
AKVQPYLDDF QKKWQEEMEL YRQKVEPLRA ELQEGARQKL HELQEKLSPL GEEMRDRARA  360
HVDALRTHLA PYLDDFQKKW QEEMELYRQK VEPLRAELQE GARQKLHELQ EKLSPLGEEM  420
RDRARAHVDA LRTHLAPYSD ELRQRLAARL EALKENGGAR LAEYHAKATE HLSTLSEKAK  480
PALEDLRQGL LPVLESFKVS FLSALEEYTK KLNTQGSGGH HHHHH                  525

SEQ ID NO: 2              moltype = AA  length = 513
FEATURE                   Location/Qualifiers
source                    1..513
                          mol_type = protein
                          organism = synthetic construct
SEQUENCE: 2
AVQIVESGGG LVQPKESLKI SCTASGFTFS NAAIYWVRQT PGKGLEWVGR IRTRPSKYAT   60
DYADSVRGRF TISRDDSKSM VYLQMDNLRT EDTAMYYCTP RATEDVPFYW GQGVMVTVSS  120
GGGGSGGGGS GGGGSDIVMT QTPSSQAVSA GEKVTMNCKS SQSVLYDENK KNYLAWYQQK  180
SGQSPKLLIY WASTGESGVP DRFIGSGSGT DFTLTISSVQ AEDLAVYYCQ QYYDFPPTFG  240
GGTKLELKAS GGGGSGGGGS DEPPQSPWDR VKDLATVYVD VLKDSGRDYV SQFEGSALGK  300
QLNLKLLDNW DSVTSTFSKL REQLGPVTQE FWDNLEKETE GLRQEMSKDL EEVKAKVQPY  360
LDDFQKKWQE EMELYRQKVE PLRAELQEGA RQKLHELQEK LSPLGEEMRD RARAHVDALR  420
THLAPYSDEL RQRLAARLEA LKENGGARLA EYHAKATEHL STLSEKAKPA LEDLRQGLLP  480
VLESFKVSFL SALEEYTKKL NTQGSGGHHH HHH                               513

SEQ ID NO: 3              moltype = AA  length = 569
FEATURE                   Location/Qualifiers
source                    1..569
                          mol_type = protein
                          organism = synthetic construct
SEQUENCE: 3
AVQIVESGGG LVQPKESLKI SCTASGFTFS NAAIYWVRQT PGKGLEWVGR IRTRPSKYAT   60
DYADSVRGRF TISRDDSKSM VYLQMDNLRT EDTAMYYCTP RATEDVPFYW GQGVMVTVSS  120
GGGGSGGGGS GGGGSDIVMT QTPSSQAVSA GEKVTMNCKS SQSVLYDENK KNYLAWYQQK  180
SGQSPKLLIY WASTGESGVP DRFIGSGSGT DFTLTISSVQ AEDLAVYYCQ QYYDFPPTFG  240
GGTKLELKAS GGGGSGGGGS KVEQAVETEP EPELRQQTEW QSGQRWELAL GRFWDYLRWV  300
QTLSEQVQEE LLSSQVTQEL RALMDETMKE LKAYKSELEE QLTPVAEETR ARLSKELQAA  360
QARLGADMED VCGRLVQYRG EVQAMLGQST EELRVRLASH LRKLRKRLLR DADDLQKRLA  420
VYQAGAREGA ERGLSAIRER LGPLVEQGRV RAATVGSLAG QPLQERAQAW GERLRARMEE  480
MGSRTRDRLD EVKEQVAEVR AKLEEQAQQI RLQAEAFQAR LKSWFEPLVE DMQRQWAGLV  540
EKVQAAVGTS AAPVPSDNHG SGGHHHHHH                                    569

SEQ ID NO: 4              moltype = AA  length = 523
FEATURE                   Location/Qualifiers
source                    1..523
                          mol_type = protein
                          organism = synthetic construct
SEQUENCE: 4
MQVQLVESGG GLVQPGGSLR LSCAASGFTF NDFYMNWIRQ PPGQAPEWLG VIRNKGNGYT   60
TEVNTSVKGR FTISRDNTQN ILYLQMNSLR AEDTAIYYCA RGGPYYYSGD DAPYWGQGVM  120
VTVSSGGGGS GGGGSGGGGS DIELTQSPSF LSTSLGNSIT ITCHASQNIK GWLAWYQQKS  180
GNAPQLLIYK ASSLQSGVPS RFSGSGSGTD YIFTISNLQP EDIATYYCQH YQSFPWTFGG  240
GTKLELKASG GGGSGGGGST FSKLREQLGP VTQEFWDNLE KETEGLRQEM SKDLEEVKAK  300
VQPYLDDFQK KWQEEMELYR QKVEPLRAEL QEGARQKLHE LQEKLSPLGE EMRDRARAHV  360
DALRTHLAPY LDDFQKKWQE EMELYRQKVE PLRAELQEGA RQKLHELQEK LSPLGEEMRD  420
RARAHVDALR THLAPYSDEL RQRLAARLEA LKENGGARLA EYHAKATEHL STLSEKAKPA  480
LEDLRQGLLP VLESFKVSFL SALEEYTKKL NTQGSGGHHH HHH                    523

SEQ ID NO: 5              moltype = AA  length = 512
FEATURE                   Location/Qualifiers
source                    1..512
                          mol_type = protein
                          organism = synthetic construct
SEQUENCE: 5
MQVQLVESGG GLVQPGGSLR LSCAASGFTF NDFYMNWIRQ PPGQAPEWLG VIRNKGNGYT   60
TEVNTSVKGR FTISRDNTQN ILYLQMNSLR AEDTAIYYCA RGGPYYYSGD DAPYWGQGVM  120
VTVSSGGGGS GGGGSGGGGS DIELTQSPSF LSTSLGNSIT ITCHASQNIK GWLAWYQQKS  180
GNAPQLLIYK ASSLQSGVPS RFSGSGSGTD YIFTISNLQP EDIATYYCQH YQSFPWTFGG  240
GTKLELKASG GGGSGGGGSD EPPQSPWDRV KDLATVYVDV LKDSGRDYVS QFEGSALGKQ  300
LNLKLLDNWD SVTSTFSKLR EQLGPVTQEF WDNLEKETEG LRQEMSKDLE EVKAKVQPYL  360
DDFQKKWQEE MELYRQKVEP LRAELQEGAR QKLHELQEKL SPLGEEMRDR ARAHVDALRT  420
HLAPYSDELR QRLAARLEAL KENGGARLAE YHAKATEHLS TLSEKAKPAL EDLRQGLLPV  480
LESFKVSFLS ALEEYTKKLN TQGSGGHHHH HH                                512
```

```
SEQ ID NO: 6           moltype = AA  length = 568
FEATURE                Location/Qualifiers
source                 1..568
                       mol_type = protein
                       organism = synthetic construct
SEQUENCE: 6
MQVQLVESGG GLVQPGGSLR LSCAASGFTF NDFYMNWIRQ PPGQAPEWLG VIRNKGNGYT   60
TEVNTSVKGR FTISRDNTQN ILYLQMNSLR AEDTAIYYCA RGGPYYYSGD DAPYWGQGVM  120
VTVSSGGGGS GGGGSGGGGS DIELTQSPSF LSTSLGNSIT ITCHASQNIK GWLAWYQQKS  180
GNAPQLLIYK ASSLQSGVPS RFSGSGSGTD YIFTISNLQP EDIATYYCQH YQSFPWTFGG  240
GTKLELKASG GGGSGGGGSK VEQAVETEPE PELRQQTEWQ SGQRWELALG RFWDYLRWVQ  300
TLSEQVQEEL LSSQVTQELR ALMDETMKEL KAYKSELEEQ LTPVAEETRA RLSKELQAAQ  360
ARLGADMEDV CGRLVQYRGE VQAMLGQSTE ELRVRLASHL RKLRKRLLRD ADDLQKRLAV  420
YQAGAREGAE RGLSAIRERL GPLVEQGRVR AATVGSLAGQ PLQERAQAWG ERLRARMEEM  480
GSRTRDRLDE VKEQVAEVRA KLEEQAQQIR LQAEAFQARL KSWFEPLVED MQRQWAGLVE  540
KVQAAVGTSA APVPSDNHGS GGHHHHHH                                    568

SEQ ID NO: 7           moltype = AA  length = 537
FEATURE                Location/Qualifiers
source                 1..537
                       mol_type = protein
                       organism = synthetic construct
SEQUENCE: 7
MAAQPAMADY KQAVVTQESA LTTSPGETVT LTCRSSTGAV TISNYANWVQ EKPDHLFTGL   60
IGGTNNRAPG VPARFSGSLI GDKAALTITG AQTEDEAIYF CALWYNNQFI FGSGTKVTVL  120
GGGGGSGGGG SGGGGSGGGG SEVQLQQSGP VLVKPGASVK MSCKASGNTF TDSFMHWMKQ  180
SHGKSLEWIG IINPYNGGTS YNQKFKGKAT LTVDKSSSTA YMELNSLTSE DSAVYYCARN  240
GVRYYFDYWG QGTTLTVSSA SGAGGGGSGG GGSTFSKLRE QLGPVTQEFW DNLEKETEGL  300
RQEEMSKDLEE VKAKVQPYLD DFQKKWQEEM ELYRQKVEPL RAELQEGARQ KLHELQEKLS  360
PLGEEMRDRA RAHVDALRTH LAPYLDDFQK KWQEEMELYR QKVEPLRAEL QEGARQKLHE  420
LQEKLSPLGE EMRDRARAHV DALRTHLAPY SDELRQRLAA RLEALKENGG ARLAEYHAKA  480
TEHLSTLSEK AKPALEDLRQ GLLPVLESFK VSFLSALEEY TKKLNTQGSG GHHHHHH     537

SEQ ID NO: 8           moltype = AA  length = 526
FEATURE                Location/Qualifiers
source                 1..526
                       mol_type = protein
                       organism = synthetic construct
SEQUENCE: 8
MAAQPAMADY KQAVVTQESA LTTSPGETVT LTCRSSTGAV TISNYANWVQ EKPDHLFTGL   60
IGGTNNRAPG VPARFSGSLI GDKAALTITG AQTEDEAIYF CALWYNNQFI FGSGTKVTVL  120
GGGGGSGGGG SGGGGSGGGG SEVQLQQSGP VLVKPGASVK MSCKASGNTF TDSFMHWMKQ  180
SHGKSLEWIG IINPYNGGTS YNQKFKGKAT LTVDKSSSTA YMELNSLTSE DSAVYYCARN  240
GVRYYFDYWG QGTTLTVSSA SGAGGGGSGG GGSDEPPQSP WDRVKDLATV YVDVLKDSGR  300
DYVSQFEGSA LGKQLNLKLL DNWDSVTSTF SKLREQLGPV TQEFWDNLEK ETEGLRQEMS  360
KDLEEVKAKV QPYLDDFQKK WQEEMELYRQ KVEPLRAELQ EGARQKLHEL QEKLSPLGEE  420
MRDRARAHVD ALRTHLAPYS DELRQRLAAR LEALKENGGA RLAEYHAKAT EHLSTLSEKA  480
KPALEDLRQG LLPVLESFKV SFLSALEEYT KKLNTQGSGG HHHHHH                526

SEQ ID NO: 9           moltype = AA  length = 582
FEATURE                Location/Qualifiers
source                 1..582
                       mol_type = protein
                       organism = synthetic construct
SEQUENCE: 9
MAAQPAMADY KQAVVTQESA LTTSPGETVT LTCRSSTGAV TISNYANWVQ EKPDHLFTGL   60
IGGTNNRAPG VPARFSGSLI GDKAALTITG AQTEDEAIYF CALWYNNQFI FGSGTKVTVL  120
GGGGGSGGGG SGGGGSGGGG SEVQLQQSGP VLVKPGASVK MSCKASGNTF TDSFMHWMKQ  180
SHGKSLEWIG IINPYNGGTS YNQKFKGKAT LTVDKSSSTA YMELNSLTSE DSAVYYCARN  240
GVRYYFDYWG QGTTLTVSSA SGAGGGGSGG GGSKVEQAVE TEPEPELRQQ TEWQSGQRWE  300
LALGRFWDYL RWVQTLSEQV QEELLSSQVT QELRALMDET MKELKAYKSE LEEQLTPVAE  360
ETRARLSKEL QAAQARLGAD MEDVCGRLVQ YRGEVQAMLG QSTEELRVRL ASHLRKLRKR  420
LLRDADDLQK RLAVYQAGAR EGAERGLSAI RERLGPLVEQ GRVRAATVGS LAGQPLQERA  480
QAWGERLRAR MEEMGSRTRD RLDEVKEQVA EVRAKLEEQA QQIRLQAEAF QARLKSWFEP  540
LVEDMQRQWA GLVEKVQAAV GTSAAPVPSD NHGSGGHHHH HH                    582

SEQ ID NO: 10          moltype = AA  length = 743
FEATURE                Location/Qualifiers
source                 1..743
                       mol_type = protein
                       organism = synthetic construct
SEQUENCE: 10
MAVQIVESGG GLVQPKESLK ISCTASGFTF SNAAIYWVRQ TPGKGLEWVG RIRTRPSKYA   60
TDYADSVRGR FTISRDDSKS MVYLQMDNLR TEDTAMYYCT PRATEDVPFY WGQGVMVTVS  120
SGGGGSGGGG SGGGGSDIVM TQTPSSQAVS AGEKVTMNCK SSQSVLYDEN KKNYLAWYQQ  180
KSGQSPKLLI YWASTGESGV PDRFIGSGSG TDFTLTISSV QAEDLAVYYC QQYYDFPPTF  240
GGGTKLELKL EPKSCDKTHT CPPCPAPELL GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
```

```
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GKASGGGGST FSKLREQLGP VTQEFWDNLE KETEGLRQEM SKDLEEVKAK VQPYLDDFQK    540
KWQEEMELYR QKVEPLRAEL QEGARQKLHE LQEKLSPLGE EMRDRARAHV DALRTHLAPY    600
LDDFQKKWQE EMELYRQKVE PLRAELQEGA RQKLHELQEK LSPLGEEMRD RARAHVDALR    660
THLAPYSDEL RQRLAARLEA LKENGGARLA EYHAKATEHL STLSEKAKPA LEDLRQGLLP    720
VLESFKVSFL SALEEYTKKL NTQ                                           743

SEQ ID NO: 11           moltype = AA   length = 732
FEATURE                 Location/Qualifiers
source                  1..732
                        mol_type = protein
                        organism = synthetic construct
SEQUENCE: 11
MAVQIVESGG GLVQPKESLK ISCTASGFTF SNAAIYWVRQ TPGKGLEWVG RIRTRPSKYA     60
TDYADSVRGR FTISRDDSKS MVYLQMDNLR TEDTAMYYCT PRATEDVPFY WGQGVMVTVS    120
SGGGGSGGGG SGGGGSDIVM TQTPSSQAVS AGEKVTMNCK SSQSVLYDEN KKNYLAWYQQ    180
KSGQSPKLLI YWASTGESGV PDRFIGSGSG TDFTLTISSV QAEDLAVYYC QQYYDFPPTF    240
GGGTKLELKL EPKSCDKTHT CPPCPAPELL GGPSVFLFPP KPKDTLMISR TPEVTCVVVD    300
VSHEDPEVKF NWYVDGVEVH NAKTKPREEQ YNSTYRVVSV LTVLHQDWLN GKEYKCKVSN    360
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GKASGGGGSD EPPQSPWDRV KDLATVYVDV LKDSGRDYVS QFEGSALGKQ LNLKLLDNWD    540
SVTSTFSKLR EQLGPVTQEF WDNLEKETEG LRQEMSKDLE EVKAKVQPYL DDFQKKWQEE    600
MELYRQKVEP LRAELQEGAR QKLHELQEKL SPLGEEMRDR ARAHVDALRT HLAPYSDELR    660
QRLAARLEAL KENGGARLAE YHAKATEHLS TLSEKAKPAL EDLRQGLLPV LESFKVSFLS    720
ALEEYTKKLN TQ                                                       732

SEQ ID NO: 12           moltype = AA   length = 788
FEATURE                 Location/Qualifiers
source                  1..788
                        mol_type = protein
                        organism = synthetic construct
SEQUENCE: 12
MAVQIVESGG GLVQPKESLK ISCTASGFTF SNAAIYWVRQ TPGKGLEWVG RIRTRPSKYA     60
TDYADSVRGR FTISRDDSKS MVYLQMDNLR TEDTAMYYCT PRATEDVPFY WGQGVMVTVS    120
SGGGGSGGGG SGGGGSDIVM TQTPSSQAVS AGEKVTMNCK SSQSVLYDEN KKNYLAWYQQ    180
KSGQSPKLLI YWASTGESGV PDRFIGSGSG TDFTLTISSV QAEDLAVYYC QQYYDFPPTF    240
GGGTKLELKL EPKSCDKTHT CPPCPAPELL GGPSVFLFPP KPKDTLMISR TPEVTCVVVD    300
VSHEDPEVKF NWYVDGVEVH NAKTKPREEQ YNSTYRVVSV LTVLHQDWLN GKEYKCKVSN    360
KALPAPIEKT ISKAKGQPRE PQVYTLPPSR DELTKNQVSL TCLVKGFYPS DIAVEWESNG    420
QPENNYKTTP PVLDSDGSFF LYSKLTVDKS RWQQGNVFSC SVMHEALHNH YTQKSLSLSP    480
GKASGGGGSK VEQAVETEPE PELRQQTEWQ SGQRWELALG RFWDYLRWVQ TLSEQVQEEL    540
LSSQVTQELR ALMDETMKEL KAYKSELEEQ LTPVAEETRA RLSKELQAAQ ARLGADMEDV    600
CGRLVQYRGE VQAMLGQSTE ELRVRLASHL RKLRKRLLRD ADDLQKRLAV YQAGAREGAE    660
RGLSAIRERL GPLVEQGRVR AATVGSLAGQ PLQERAQAWG ERLRARMEEM GSRTRDRLDE    720
VKEQVAEVRA KLEEQAQQIR LQAEAFQARL KSWFEPLVED MQRQWAGLVE KVQAAVGTSA    780
APVPSDNH                                                            788

SEQ ID NO: 13           moltype = AA   length = 741
FEATURE                 Location/Qualifiers
source                  1..741
                        mol_type = protein
                        organism = synthetic construct
SEQUENCE: 13
MQVQLVESGG GLVQPGGSLR LSCAASGFTF NDFYMNWIRQ PPGQAPEWLG VIRNKGNGYT     60
TEVNTSVKGR FTISRDNTQN ILYLQMNSLR AEDTAIYYCA RGGPYYYSGD DAPYWGQGVM    120
VTVSSGGGGS GGGGSGGGGS DIELTQSPSF LSTSLGNSIT ITCHASQNIK GWLAWYQQKS    180
GNAPQLLIYK ASSLQSGVPS RFSGSGSGTD YIFTISNLQP EDIATYYCQH YQSFPWTFGG    240
GTKLELKLEP KSCDKTHTCP PCPAPELLGG PSVFLFPPKP KDTLMISRTP EVTCVVVDVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSRDE LTKNQVSLTC LVKGFYPSDI AVEWESNGQP    420
ENNYKTTPPV LDSDGSFFLY SKLTVDKSRW QQGNVFSCSV MHEALHNHYT QKSLSLSPGK    480
ASGGGGSTFS KLREQLGPVT QEFWDNLEKE TEGLRQEMSK DLEEVKAKVQ PYLDDFQKKW    540
QEEMELYRQK VEPLRAELQE GARQKLHELQ EKLSPLGEEM RDRARAHVDA LRTHLAPYLD    600
DFQKKWQEEM ELYRQKVEPL RAELQEGARQ KLHELQEKLS PLGEEMRDRA RAHVDALRTH    660
LAPYSDELRQ RLAARLEALK ENGGARLAEY HAKATEHLST LSEKAKPALE DLRQGLLPVL    720
ESFKVSFLSA LEEYTKKLNT Q                                             741

SEQ ID NO: 14           moltype = AA   length = 730
FEATURE                 Location/Qualifiers
source                  1..730
                        mol_type = protein
                        organism = synthetic construct
SEQUENCE: 14
MQVQLVESGG GLVQPGGSLR LSCAASGFTF NDFYMNWIRQ PPGQAPEWLG VIRNKGNGYT     60
TEVNTSVKGR FTISRDNTQN ILYLQMNSLR AEDTAIYYCA RGGPYYYSGD DAPYWGQGVM    120
VTVSSGGGGS GGGGSGGGGS DIELTQSPSF LSTSLGNSIT ITCHASQNIK GWLAWYQQKS    180
GNAPQLLIYK ASSLQSGVPS RFSGSGSGTD YIFTISNLQP EDIATYYCQH YQSFPWTFGG    240
```

```
GTKLELKLEP KSCDKTHTCP PCPAPELLGG PSVFLFPPKP KDTLMISRTP EVTCVVVDVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSRDE LTKNQVSLTC LVKGFYPSDI AVEWESNGQP    420
ENNYKTTPPV LDSDGSFFLY SKLTVDKSRW QQGNVFSCSV MHEALHNHYT QKSLSLSPGK    480
ASGGGGSDEP PQSPWDRVKD LATVYVDVLK DSGRDYVSQF EGSALGKQLN LKLLDNWDSV    540
TSTFSKLREQ LGPVTQEFWD NLEKETEGLR QEMSKDLEEV KAKVQPYLDD FQKKWQEEME    600
LYRQKVEPLR AELQEGARQK LHELQEKLSP LGEEMRDRAR AHVDALRTHL APYSDELRQR    660
LAARLEALKE NGGARLAEYH AKATEHLSTL SEKAKPALED LRQGLLPVLE SFKVSFLSAL    720
EEYTKKLNTQ                                                          730

SEQ ID NO: 15           moltype = AA length = 786
FEATURE                 Location/Qualifiers
source                  1..786
                        mol_type = protein
                        organism = synthetic construct
SEQUENCE: 15
MQVQLVESGG GLVQPGGSLR LSCAASGFTF NDFYMNWIRQ PPGQAPEWLG VIRNKGNGYT     60
TEVNTSVKGR FTISRDNTQN ILYLQMNSLR AEDTAIYYCA RGGPYYYSGD DAPYWGQGVM    120
VTVSSGGGGS GGGGSGGGGS DIELTQSPSF LSTSLGNSIT ITCHASQNIK GWLAWYQQKS    180
GNAPQLLIYK ASSLQSGVPS RFSGSGSGTD YIFTISNLQP EDIATYYCQH YQSFPWTFGG    240
GTKLELKLEP KSCDKTHTCP PCPAPELLGG PSVFLFPPKP KDTLMISRTP EVTCVVVDVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSRDE LTKNQVSLTC LVKGFYPSDI AVEWESNGQP    420
ENNYKTTPPV LDSDGSFFLY SKLTVDKSRW QQGNVFSCSV MHEALHNHYT QKSLSLSPGK    480
ASGGGGSKVE QAVETEPEPE LRQQTEWQSG QRWELALGRF WDYLRWVQTL SEQVQEEELLS   540
SQVTQELRAL MDETMKELKA YKSELEEQLT PVAEETRARL SKELQAAQAR LGADMEDVCG    600
RLVQYRGEVQ AMLGOSTEEL RVRLASHLRK LRKRLLRDAD DLQKRLAVYQ AGAREGAERG    660
LSAIRERLGP LVEQGRVRAA TVGSLAGQPL QERAQAWGER LRARMEEMGS RTRDRLDEVK    720
EQVAEVRAKL EEQAQQIRLQ AEAFQARLKS WFEPLVEDMQ RQWAGLVEKV QAAVGTSAAP    780
VPSDNH                                                              786

SEQ ID NO: 16           moltype = AA length = 757
FEATURE                 Location/Qualifiers
source                  1..757
                        mol_type = protein
                        organism = synthetic construct
SEQUENCE: 16
MAAQPAMADY KQAVVTQESA LTTSPGETVT LTCRSSTGAV TISNYANWVQ EKPDHLFTGL     60
IGGTNNRAPG VPARFSGSLI GDKAALTITG AQTEDEAIYF CALWYNNQFI FGSGTKVTVL    120
GGGGGSGGGG SGGGGSGGGG SEVQLQQSGP VLVKPGASVK MSCKASGNTF TDSFMHWMKQ    180
SHGKSLEWIG IINPYNGGTS YNQKFKGKAT LTVDKSSSTA YMELNSLTSE DSAVYYCARN    240
GVRYYFDYWG QGTTLTVSSA SGALEPKSCD KTHTCPPCPA PELLGGPSVF LFPPKPKDTL    300
MISRTPEVTC VVVDVSHEDP EVKFNWYVDG VEVHNAKTKP REEQYNSTYR VVSVLTVLHQ    360
DWLNGKEYKC KVSNKALPAP IEKTISKAKG QPREPQVYTL PPSRDELTKN QVSLTCLVKG    420
FYPSDIAVEW ESNGQPENNY KTTPPVLDSD GSFFLYSKLT VDKSRWQQGN VFSCSVMHEA    480
LHNHYTQKSL SLSPGKASGG GGSTFSKLRE QLGPVTQEFW DNLEKETEGL RQEMSKDLEE    540
VKAKVQPYLD DFQKKWQEEM ELYRQKVEPL RAELQEGARQ KLHELQEKLS PLGEEMRDRA    600
RAHVDALRTH LAPYLDDFQK KWQEEMELYR QKVEPLRAEL QEGARQKLHE LQEKLSPLGE    660
EMRDRARAHV DALRTHLAPY SDELRQRLAA RLEALKENGG ARLAEYHAKA TEHLSTLSEK    720
AKPALEDLRQ GLLPVLESFK VSFLSALEEY TKKLNTQ                             757

SEQ ID NO: 17           moltype = AA length = 746
FEATURE                 Location/Qualifiers
source                  1..746
                        mol_type = protein
                        organism = synthetic construct
SEQUENCE: 17
MAAQPAMADY KQAVVTQESA LTTSPGETVT LTCRSSTGAV TISNYANWVQ EKPDHLFTGL     60
IGGTNNRAPG VPARFSGSLI GDKAALTITG AQTEDEAIYF CALWYNNQFI FGSGTKVTVL    120
GGGGGSGGGG SGGGGSGGGG SEVQLQQSGP VLVKPGASVK MSCKASGNTF TDSFMHWMKQ    180
SHGKSLEWIG IINPYNGGTS YNQKFKGKAT LTVDKSSSTA YMELNSLTSE DSAVYYCARN    240
GVRYYFDYWG QGTTLTVSSA SGALEPKSCD KTHTCPPCPA PELLGGPSVF LFPPKPKDTL    300
MISRTPEVTC VVVDVSHEDP EVKFNWYVDG VEVHNAKTKP REEQYNSTYR VVSVLTVLHQ    360
DWLNGKEYKC KVSNKALPAP IEKTISKAKG QPREPQVYTL PPSRDELTKN QVSLTCLVKG    420
FYPSDIAVEW ESNGQPENNY KTTPPVLDSD GSFFLYSKLT VDKSRWQQGN VFSCSVMHEA    480
LHNHYTQKSL SLSPGKASGG GGSDEPPQSP WDRVKDLATV YVDVLKDSGR DYVSQFEGSA    540
LGKQLNLKLL DNWDSVTSTF SKLREQLGPV TQEFWDNLEK ETEGLRQEMS KDLEEVKAKV    600
QPYLDDFQKK WQEEMELYRQ KVEPLRAELQ EGARQKLHEL QEKLSPLGEE MRDRARAHVD    660
ALRTHLAPYS DELRQRLAAR LEALKENGGA RLAEYHAKAT EHLSTLSEKA KPALEDLRQG    720
LLPVLESFKV SFLSALEEYT KKLNTQ                                         746

SEQ ID NO: 18           moltype = AA length = 802
FEATURE                 Location/Qualifiers
source                  1..802
                        mol_type = protein
                        organism = synthetic construct
SEQUENCE: 18
MAAQPAMADY KQAVVTQESA LTTSPGETVT LTCRSSTGAV TISNYANWVQ EKPDHLFTGL     60
IGGTNNRAPG VPARFSGSLI GDKAALTITG AQTEDEAIYF CALWYNNQFI FGSGTKVTVL    120
```

```
GGGGGSGGGG  SGGGGSGGGG  SEVQLQQSGP  VLVKPGASVK  MSCKASGNTF  TDSFMHWMKQ   180
SHGKSLEWIG  IINPYNGGTS  YNQKFKGKAT  LTVDKSSSTA  YMELNSLTSE  DSAVYYCARN   240
GVRYYFDYWG  QGTTLTVSSA  SGALEPKSCD  KTHTCPPCPA  PELLGGPSVF  LFPPKPKDTL   300
MISRTPEVTC  VVVDVSHEDP  EVKFNWYVDG  VEVHNAKTKP  REEQYNSTYR  VVSVLTVLHQ   360
DWLNGKEYKC  KVSNKALPAP  IEKTISKAKG  QPREPQVYTL  PPSRDELTKN  QVSLTCLVKG   420
FYPSDIAVEW  ESNGQPENNY  KTTPPVLDSD  GSFFLYSKLT  VDKSRWQQGN  VFSCSVMHEA   480
LHNHYTQKSL  SLSPGKASGG  GGSKVEQAVE  TEPEPELRQQ  TEWQSGQRWE  LALGRFWDYL   540
RWVQTLSEQV  QEELLSSQVT  QELRALMDET  MKELKAYKSE  LEEQLTPVAE  ETRARLSKEL   600
QAAQARLGAD  MEDVCGRLVQ  YRGEVQAMLG  QSTEELRVRL  ASHLRKLRKR  LLRDADDLQK   660
RLAVYQAGAR  EGAERGLSAI  RERLGPLVEQ  GRVRAATVGS  LAGQPLQERA  QAWGERLRAR   720
MEEMGSRTRD  RLDEVKEQVA  EVRAKLEEQA  QQIRLQAEAF  QARLKSWFEP  LVEDMQRQWA   780
GLVEKVQAAV  GTSAAPVPSD  NH                                              802

SEQ ID NO: 19           moltype = AA   length = 220
FEATURE                 Location/Qualifiers
source                  1..220
                        mol_type = protein
                        organism = synthetic construct
SEQUENCE: 19
MDIVMTQTPS  SQAVSAGEKV  TMNCKSSQSV  LYDENKKNYL  AWYQQKSGQS  PKLLIYWAST    60
GESGVPDRFI  GSGSGTDFTL  TISSVQAEDL  AVYYCQQYYD  FPPTFGGGTK  LELKTVAAPS   120
VFIFPPSDEQ  LKSGTASVVC  LLNNFYPREA  KVQWKVDNAL  QSGNSQESVT  EQDSKDSTYS   180
LSSTLTLSKA  DYEKHKVYAC  EVTHQGLSSP  VTKSFNRGEC                           220

SEQ ID NO: 20           moltype = AA   length = 214
FEATURE                 Location/Qualifiers
source                  1..214
                        mol_type = protein
                        organism = synthetic construct
SEQUENCE: 20
MDIELTQSPS  FLSTSLGNSI  TITCHASQNI  KGWLAWYQQK  SGNAPQLLIY  KASSLQSGVP    60
SRFSGSGSGT  DYIFTISNLQ  PEDIATYYCQ  HYQSFPWTFG  GGTKLELKTV  AAPSVFIFPP   120
SDEQLKSGTA  SVVCLLNNFY  PREAKVQWKV  DNALQSGNSQ  ESVTEQDSKD  STYSLSSTLT   180
LSKADYEKHK  VYACEVTHQG  LSSPVTKSFN  RGEC                                 214

SEQ ID NO: 21           moltype = AA   length = 227
FEATURE                 Location/Qualifiers
source                  1..227
                        mol_type = protein
                        organism = synthetic construct
SEQUENCE: 21
MAAQPAMADY  KQAVVTQESA  LTTSPGETVT  LTCRSSTGAV  TISNYANWVQ  EKPDHLFTGL    60
IGGTNNRAPG  VPARFSGSLI  GDKAALTITG  AQTEDEAIYF  CALWYNNQFI  FGSGTKVTVL   120
GTVAAPSVFI  FPPSDEQLKS  GTASVVCLLN  NFYPREAKVQ  WKVDNALQSG  NSQESVTEQD   180
SKDSTYSLSS  TLTLSKADYE  KHKVYACEVT  HQGLSSPVTK  SFNRGEC                  227

SEQ ID NO: 22           moltype = AA   length = 711
FEATURE                 Location/Qualifiers
source                  1..711
                        mol_type = protein
                        organism = synthetic construct
SEQUENCE: 22
MAVQIVESGG  GLVQPKESLK  ISCTASGFTF  SNAAIYWVRQ  TPGKGLEWVG  RIRTRPSKYA    60
TDYADSVRGR  FTISRDDSKS  MVYLQMDNLR  TEDTAMYYCT  PRATEDVPFY  WGQGVMVTVS   120
SASTKGPSVF  PLAPSSKSTS  GGTAALGCLV  KDYFPEPVTV  SWNSGALTSG  VHTFPAVLQS   180
SGLYSLSSVV  TVPSSSLGTQ  TYICNVNHKP  SNTKVDKKVE  PPKSCDKTHT  CPPCPAPELL   240
GGPSVFLFPP  KPKDTLMISR  TPEVTCVVVD  VSHEDPEVKF  NWYVDGVEVH  NAKTKPREEQ   300
YNSTYRVVSV  LTVLHQDWLN  GKEYKCKVSN  KALPAPIEKT  ISKAKGQPRE  PQVYTLPPSR   360
DELTKNQVSL  TCLVKGFYPS  DIAVEWESNG  QPENNYKTTP  PVLDSDGSFF  LYSKLTVDKS   420
RWQQGNVFSC  SVMHEALHNH  YTQKSLSLSP  GKGGGGSTFS  KLREQLGPVT  QEFWDNLEKE   480
TEGLRQEMSK  DLEEVKAKVQ  PYLDDFQKKW  QEEMELYRQK  VEPLRAELQE  GARQKLHELQ   540
EKLSPLGEEM  RDRARAHVDA  LRTHLAPYLD  DFQKKWQEEM  ELYRQKVEPL  RAELQEGARQ   600
KLHELQEKLS  PLGEEMRDRA  RAHVDALRTH  LAPYSDELRQ  RLAARLEALK  ENGGARLAEY   660
HAKATEHLST  LSEKAKPALE  DLRQGLLPVL  ESFKVSFLSA  LEEYTKKLNT  Q            711

SEQ ID NO: 23           moltype = AA   length = 700
FEATURE                 Location/Qualifiers
source                  1..700
                        mol_type = protein
                        organism = synthetic construct
SEQUENCE: 23
MAVQIVESGG  GLVQPKESLK  ISCTASGFTF  SNAAIYWVRQ  TPGKGLEWVG  RIRTRPSKYA    60
TDYADSVRGR  FTISRDDSKS  MVYLQMDNLR  TEDTAMYYCT  PRATEDVPFY  WGQGVMVTVS   120
SASTKGPSVF  PLAPSSKSTS  GGTAALGCLV  KDYFPEPVTV  SWNSGALTSG  VHTFPAVLQS   180
SGLYSLSSVV  TVPSSSLGTQ  TYICNVNHKP  SNTKVDKKVE  PPKSCDKTHT  CPPCPAPELL   240
GGPSVFLFPP  KPKDTLMISR  TPEVTCVVVD  VSHEDPEVKF  NWYVDGVEVH  NAKTKPREEQ   300
YNSTYRVVSV  LTVLHQDWLN  GKEYKCKVSN  KALPAPIEKT  ISKAKGQPRE  PQVYTLPPSR   360
DELTKNQVSL  TCLVKGFYPS  DIAVEWESNG  QPENNYKTTP  PVLDSDGSFF  LYSKLTVDKS   420
RWQQGNVFSC  SVMHEALHNH  YTQKSLSLSP  GKGGGGSDEP  PQSPWDRVKD  LATVYVDLKN   480
```

```
DSGRDYVSQF EGSALGKQLN LKLLDNWDSV TSTFSKLREQ LGPVTQEFWD NLEKETEGLR   540
QEMSKDLEEV KAKVQPYLDD FQKKWQEEME LYRQKVEPLR AELQEGARQK LHELQEKLSP   600
LGEEMRDRAR AHVDALRTHL APYSDELRQR LAARLEALKE NGGARLAEYH AKATEHLSTL   660
SEKAKPALED LRQGLLPVLE SFKVSFLSAL EEYTKKLNTQ                         700

SEQ ID NO: 24           moltype = AA  length = 756
FEATURE                 Location/Qualifiers
source                  1..756
                        mol_type = protein
                        organism = synthetic construct
SEQUENCE: 24
MAVQIVESGG GLVQPKESLK ISCTASGFTF SNAAIYWVRQ TPGKGLEWVG RIRTRPSKYA    60
TDYADSVRGR FTISRDDSKS MVYLQMDNLR TEDTAMYYCT PRATEDVPFY WGQGVMVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKGGGGSKVE QAVETEPEPE LRQQTEWQSG   480
QRWELALGRF WDYLRWVQTL SEQVQEELLS SQVTQELRAL MDETMKELKA YKSELEEQLT   540
PVAEETRARL SKELQAAQAR LGADMEDVCG RLVQYRGEVQ AMLGQSTEEL RVRLASHLRK   600
LRKRLLRDAD DLQKRLAVYQ AGAREGAERG LSAIRERLGP LVEQGRVRAA TVGSLAGQPL   660
QERAQAWGER LRARMEEMGS RTRDRLDEVK EQVAEVRAKL EEQAQQIRLQ AEAFQARLKS   720
WFEPLVEDMQ RQWAGLVEKV QAAVGTSAAP VPSDNH                            756

SEQ ID NO: 25           moltype = AA  length = 715
FEATURE                 Location/Qualifiers
source                  1..715
                        mol_type = protein
                        organism = synthetic construct
SEQUENCE: 25
MQVQLVESGG GLVQPGGSLR LSCAASGFTF NDFYMNWIRQ PPGQAPEWLG VIRNKGNGYT    60
TEVNTSVKGR FTISRDNTQN ILYLQMNSLR AEDTAIYYCA RGGPYYYSGD DAPYWGQGVM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGKGGGG STFSKLREQL GPVTQEFWDN   480
LEKETEGLRQ EMSKDLEEVK AKVQPYLDDF QKKWQEEMEL YRQKVEPLRA ELQEGARQKL   540
HELQEKLSPL GEEMRDRARA HVDALRTHLA PYLDDFQKKW QEEMELYRQK VEPLRAELQE   600
GARQKLHELQ EKLSPLGEEM RDRARAHVDA LRTHLAPYSD ELRQRLAARL EALKENGGAR   660
LAEYHAKATE HLSTLSEKAK PALEDLRQGL LPVLESFKVS FLSALEEYTK KLNTQ        715

SEQ ID NO: 26           moltype = AA  length = 704
FEATURE                 Location/Qualifiers
source                  1..704
                        mol_type = protein
                        organism = synthetic construct
SEQUENCE: 26
MQVQLVESGG GLVQPGGSLR LSCAASGFTF NDFYMNWIRQ PPGQAPEWLG VIRNKGNGYT    60
TEVNTSVKGR FTISRDNTQN ILYLQMNSLR AEDTAIYYCA RGGPYYYSGD DAPYWGQGVM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGKGGGG SDEPPQSPWD RVKDLATYV   480
DVLKDSGRDY VSQFEGSALG KQLNLKLLDN WDSVTSTFSK LREQLGPVTQ EFWDNLEKET   540
EGLRQEMSKD LEEVKAKVQP YLDDFQKKWQ EEMELYRQKV EPLRAELQEG ARQKLHELQE   600
KLSPLGEEMR DRARAHVDAL RTHLAPYSDE LRQRLAARLE ALKENGGARL AEYHAKATEH   660
LSTLSEKAKP ALEDLRQGLL PVLESFKVSF LSALEEYTKK LNTQ                    704

SEQ ID NO: 27           moltype = AA  length = 760
FEATURE                 Location/Qualifiers
source                  1..760
                        mol_type = protein
                        organism = synthetic construct
SEQUENCE: 27
MQVQLVESGG GLVQPGGSLR LSCAASGFTF NDFYMNWIRQ PPGQAPEWLG VIRNKGNGYT    60
TEVNTSVKGR FTISRDNTQN ILYLQMNSLR AEDTAIYYCA RGGPYYYSGD DAPYWGQGVM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPSRDELTKN QVSLTCLVKG FYPSDIAVEW ESNGQPENNY KTTPPVLDSD GSFFLYSKLT   420
VDKSRWQQGN VFSCSVMHEA LHNHYTQKSL SLSPGKGGGG SKVEQAVETE PEPELRQQTE   480
WQSGQRWELA LGRFWDYLRW VQTLSEQVQE ELLSSQVTQE LRALMDETMK ELKAYKSELE   540
EQLTPVAEET RARLSKELQA AQARLGADME DVCGRLVQYR GEVQAMLGQS TEELRVRLAS   600
```

```
HLRKLRKRLL  RDADDLQKRL  AVYQAGAREG  AERGLSAIRE  RLGPLVEQGR  VRAATVGSLA   660
GQPLQERAQA  WGERLRARME  EMGSRTRDRL  DEVKEQVAEV  RAKLEEQAQQ  IRLQAEAFQA   720
RLKSWFEPLV  EDMQRQWAGL  VEKVQAAVGT  SAAPVPSDNH                          760

SEQ ID NO: 28           moltype = AA   length = 713
FEATURE                 Location/Qualifiers
source                  1..713
                        mol_type = protein
                        organism = synthetic construct
SEQUENCE: 28
MEVQLQQSGP  VLVKPGASVK  MSCKASGNTF  TDSFMHWMKQ  SHGKSLEWIG  IINPYNGGTS    60
YNQKFKGKAT  LTVDKSSSTA  YMELNSLTSE  DSAVYYCARN  GVRYYFDYWG  QGTTLTVSSA   120
SGAASTKGPS  VFPLAPSSKS  TSGGTAALGC  LVKDYFPEPV  TVSWNSGALT  SGVHTFPAVL   180
QSSGLYSLSS  VVTVPSSLG   TQTYICNVNH  KPSNTKVDKK  VEPPKSCDKT  HTCPPCPAPE   240
LLGGPSVFLF  PPKPKDTLMI  SRTPEVTCVV  VDVSHEDPEV  KFNWYVDGVE  VHNAKTKPRE   300
EQYNSTYRVV  SVLTVLHQDW  LNGKEYKCKV  SNKALPAPIE  KTISKAKGQP  REPQVYTLPP   360
SRDELTKNQV  SLTCLVKGFY  PSDIAVEWES  NGQPENNYKT  TPPVLDSDGS  FFLYSKLTVD   420
KSRWQQGNVF  SCSVMHEALH  NHYTQKSLSL  SPGKGGGGST  FSKLREQLGP  VTQEFWDNLE   480
KETEGLRQEM  SKDLEEVKAK  VQPYLDDFQK  KWQEEMELYR  QKVEPLRAEL  QEGARQKLHE   540
LQEKLSPLGE  EMRDRARAHV  DALRTHLAPY  LDDFQKKWQE  EMELYRQKVE  PLRAELQEGA   600
RQKLHELQEK  LSPLGEEMRD  RARAHVDALR  THLAPYSDEL  RQRLAARLEA  LKENGGARLA   660
EYHAKATEHL  STLSEKAKPA  LEDLRQGLLP  VLESFKVSFL  SALEEYTKKL  NTQ          713

SEQ ID NO: 29           moltype = AA   length = 702
FEATURE                 Location/Qualifiers
source                  1..702
                        mol_type = protein
                        organism = synthetic construct
SEQUENCE: 29
MEVQLQQSGP  VLVKPGASVK  MSCKASGNTF  TDSFMHWMKQ  SHGKSLEWIG  IINPYNGGTS    60
YNQKFKGKAT  LTVDKSSSTA  YMELNSLTSE  DSAVYYCARN  GVRYYFDYWG  QGTTLTVSSA   120
SGAASTKGPS  VFPLAPSSKS  TSGGTAALGC  LVKDYFPEPV  TVSWNSGALT  SGVHTFPAVL   180
QSSGLYSLSS  VVTVPSSLG   TQTYICNVNH  KPSNTKVDKK  VEPPKSCDKT  HTCPPCPAPE   240
LLGGPSVFLF  PPKPKDTLMI  SRTPEVTCVV  VDVSHEDPEV  KFNWYVDGVE  VHNAKTKPRE   300
EQYNSTYRVV  SVLTVLHQDW  LNGKEYKCKV  SNKALPAPIE  KTISKAKGQP  REPQVYTLPP   360
SRDELTKNQV  SLTCLVKGFY  PSDIAVEWES  NGQPENNYKT  TPPVLDSDGS  FFLYSKLTVD   420
KSRWQQGNVF  SCSVMHEALH  NHYTQKSLSL  SPGKGGGGSD  EPPQSPWDRV  KDLATVYVDV   480
LKDSGRDYVS  QFEGSALGKQ  LNLKLLDNWD  SVTSTFSKLR  EQLGPVTQEF  WDNLEKETEG   540
LRQEMSKDLE  EVKAKVQPYL  DDFQKKWQEE  MELYRQKVEP  LRAELQEGAR  QKLHELQEKL   600
SPLGEEMRDR  ARAHVDALRT  HLAPYSDELR  QRLAARLEAL  KENGGARLAE  YHAKATEHLS   660
TLSEKAKPAL  EDLRQGLLPV  LESFKVSFLS  ALEEYTKKLN  TQ                       702

SEQ ID NO: 30           moltype = AA   length = 758
FEATURE                 Location/Qualifiers
source                  1..758
                        mol_type = protein
                        organism = synthetic construct
SEQUENCE: 30
MEVQLQQSGP  VLVKPGASVK  MSCKASGNTF  TDSFMHWMKQ  SHGKSLEWIG  IINPYNGGTS    60
YNQKFKGKAT  LTVDKSSSTA  YMELNSLTSE  DSAVYYCARN  GVRYYFDYWG  QGTTLTVSSA   120
SGAASTKGPS  VFPLAPSSKS  TSGGTAALGC  LVKDYFPEPV  TVSWNSGALT  SGVHTFPAVL   180
QSSGLYSLSS  VVTVPSSLG   TQTYICNVNH  KPSNTKVDKK  VEPPKSCDKT  HTCPPCPAPE   240
LLGGPSVFLF  PPKPKDTLMI  SRTPEVTCVV  VDVSHEDPEV  KFNWYVDGVE  VHNAKTKPRE   300
EQYNSTYRVV  SVLTVLHQDW  LNGKEYKCKV  SNKALPAPIE  KTISKAKGQP  REPQVYTLPP   360
SRDELTKNQV  SLTCLVKGFY  PSDIAVEWES  NGQPENNYKT  TPPVLDSDGS  FFLYSKLTVD   420
KSRWQQGNVF  SCSVMHEALH  NHYTQKSLSL  SPGKGGGGSK  VEQAVETEPE  PELRQQTEWQ   480
SGQRWELALG  RFWDYLRWVQ  TLSEQVQEEL  LSSQVTQELR  ALMDETMKEL  KAYKSELEEQ   540
LTPVAEETRA  RLSKELQAAQ  ARLGADMEDV  CGRLVQYRGE  VQAMLGQSTE  ELRVRLASHL   600
RKLRKRLLRD  ADDLQKRLAV  YQAGAREGAE  RGLSAIRERL  GPLVEQGRVR  AATVGSLAGQ   660
PLQERAQAWG  ERLRARMEEM  GSRTRDRLDE  VKEQVAEVRA  KLEEQAQQIR  LQAEAFQARL   720
KSWFEPLVED  MQRQWAGLVE  KVQAAVGTSA  APVPSDNH                            758
```